United States Patent
Claffey et al.

(10) Patent No.: US 10,457,726 B2
(45) Date of Patent: Oct. 29, 2019

(54) ANTIBODY AND ANTIGEN-BINDING FRAGMENT COMPOSITIONS TARGETING CELL SURFACE ANTIGENS IN TUMORS AND METHODS OF USE THEREOF

(71) Applicant: UNIVERSITY OF CONNECTICUT, Farmington, CT (US)

(72) Inventors: Kevin P. Claffey, Burlington, CT (US); Charan Devarakonda, Willimantic, CT (US); Daniel Kita, Cheshire, CT (US)

(73) Assignee: UNIVERSITY OF CONNECTICUT, Farmington, CT (US)

( * ) Notice: Subject to any disclaimer, the term of this patent is extended or adjusted under 35 U.S.C. 154(b) by 90 days.

(21) Appl. No.: 15/637,402

(22) Filed: Jun. 29, 2017

(65) Prior Publication Data

US 2018/0002412 A1 Jan. 4, 2018

Related U.S. Application Data

(60) Provisional application No. 62/356,813, filed on Jun. 30, 2016.

(51) Int. Cl.

| | |
|---|---|
| *C07K 16/18* | (2006.01) |
| *G01N 33/574* | (2006.01) |
| *A61K 39/00* | (2006.01) |
| *C07K 16/28* | (2006.01) |
| *C07K 16/30* | (2006.01) |

(52) U.S. Cl.
CPC .............. *C07K 16/18* (2013.01); *C07K 16/28* (2013.01); *C07K 16/3015* (2013.01); *G01N 33/57492* (2013.01); *A61K 2039/505* (2013.01); *C07K 2317/565* (2013.01); *C07K 2317/569* (2013.01); *C07K 2317/76* (2013.01)

(58) Field of Classification Search
None
See application file for complete search history.

(56) References Cited

U.S. PATENT DOCUMENTS

| | | |
|---|---|---|
| 8,729,249 B2 | 5/2014 | Goetsch et al. |
| 8,846,036 B2 | 9/2014 | Birkenmeyer et al. |
| 8,883,149 B2 | 11/2014 | Sela et al. |
| 9,499,603 B2 | 11/2016 | Tyson |
| 2011/0150881 A1 | 6/2011 | Jay et al. |
| 2013/0243802 A1 | 9/2013 | Griffiths et al. |

FOREIGN PATENT DOCUMENTS

EP 1818062 A1 8/2007

OTHER PUBLICATIONS

Devarakonda et al (BMC Cancer, 2015, 15:614; internet pp. 1-19; published Sep. 3, 2015).*
Devarakonda et al.; "Patient-Derived Heavy Chain Antibody Targets Cell Surface HSP90 on Breast Tumors"; BMC Cancer; 15; pp. 614-623; (2015).
Rodriguez-Pinto et al.; "Identification of Novel Tumor Antigens with Patient-Derived Immune-Selected Antibodies"; Cancer Immunol Immunother; 58; pp. 221-234; (2009).

* cited by examiner

*Primary Examiner* — Laura B Goddard
(74) *Attorney, Agent, or Firm* — Cantor Colburn LLP

(57) ABSTRACT

Described herein is an isolated antibody or antigen-binding fragment including a heavy chain variable region including three heavy chain complementary determining regions (HCDRs), wherein the sequence of HCDR1 is GYRLSELS (SEQ ID NO: 1), the sequence of HCDR2 is ISGWDGNT (SEQ ID NO: 2), and the sequence of HCDR3 is ARASGYNY(SEQ ID NO: 3), wherein the isolated antibody or antigen-binding fragment specifically binds human HSP90, specifically HSP90 beta. Also included are detection and therapeutic methods using the isolated antibodies or antigen-binding fragments.

17 Claims, 11 Drawing Sheets
(9 of 11 Drawing Sheet(s) Filed in Color)
Specification includes a Sequence Listing.

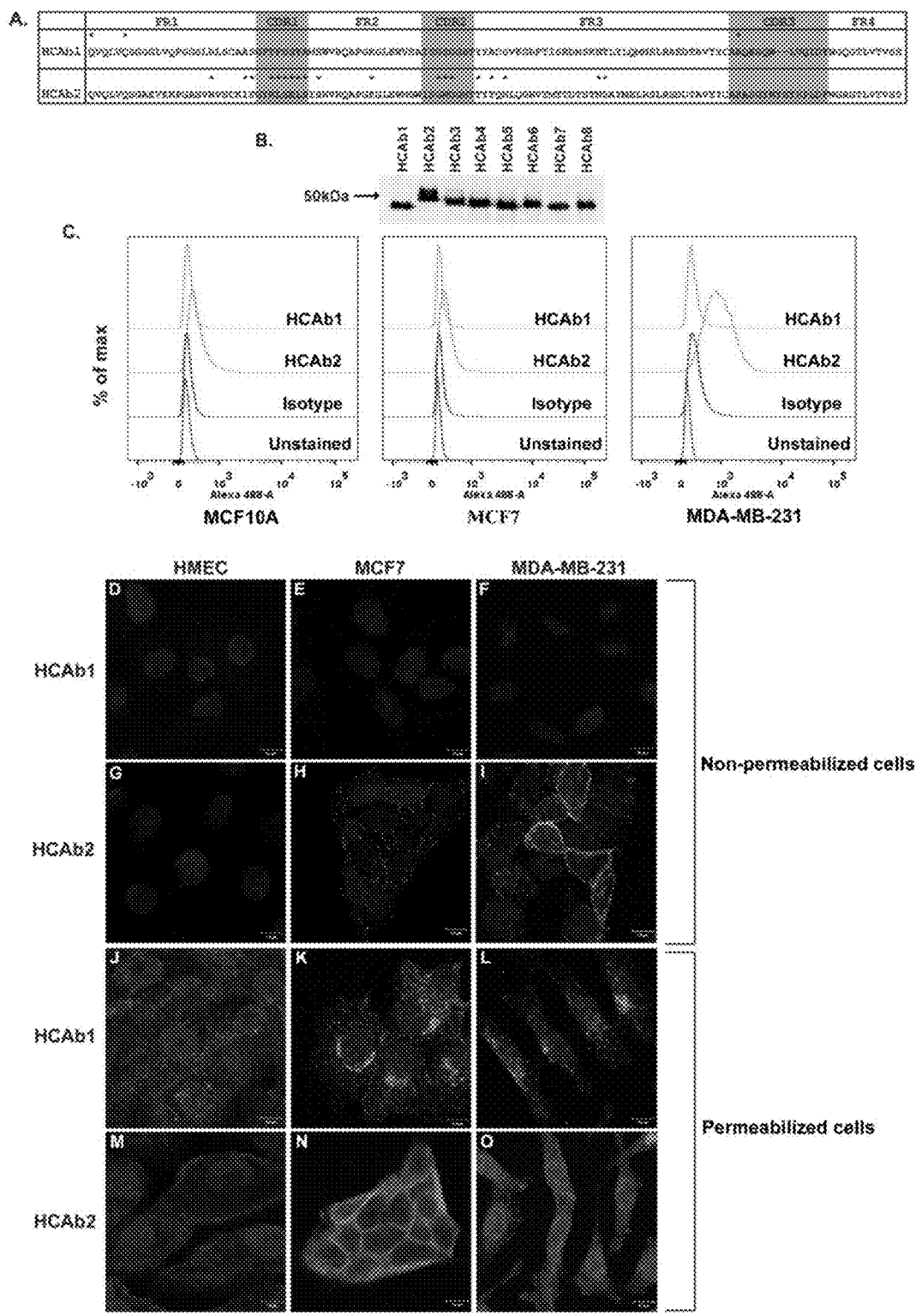
FIGURE 1 A-O

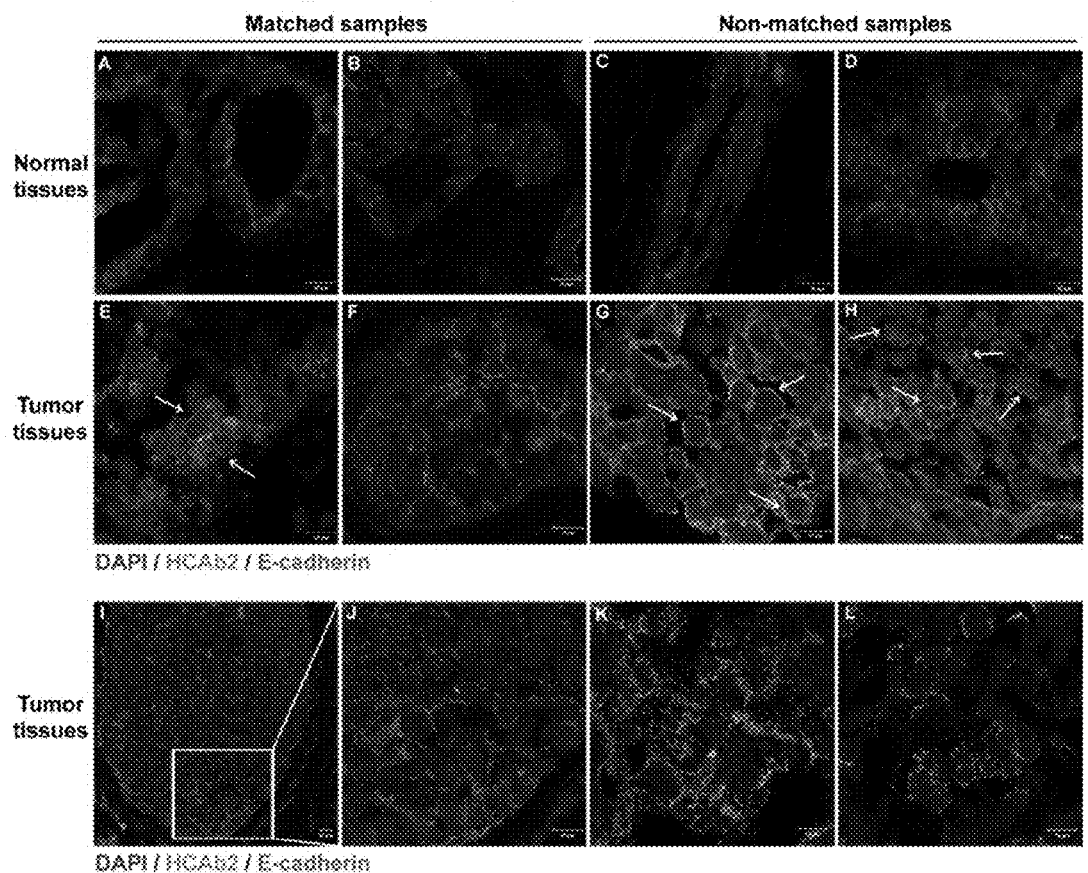
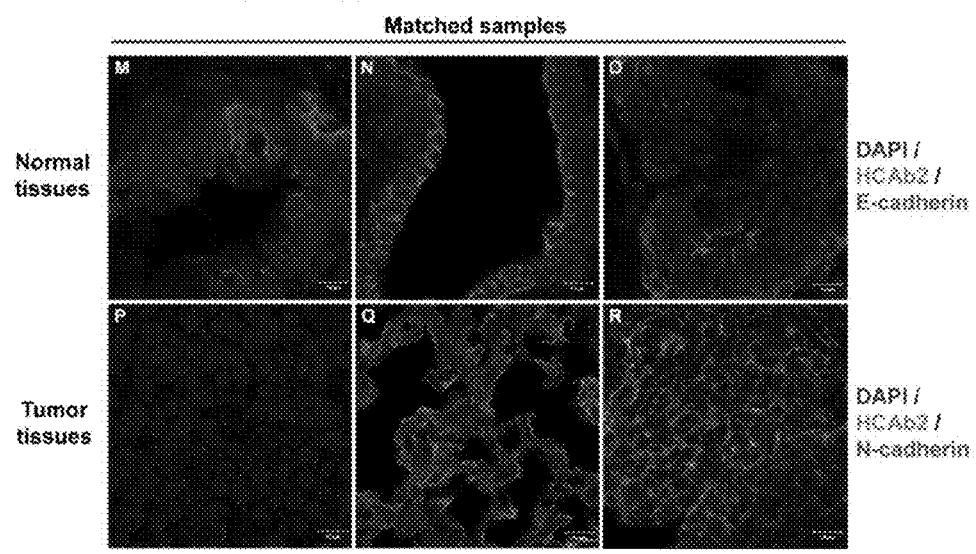
FIGURE 2 A-R

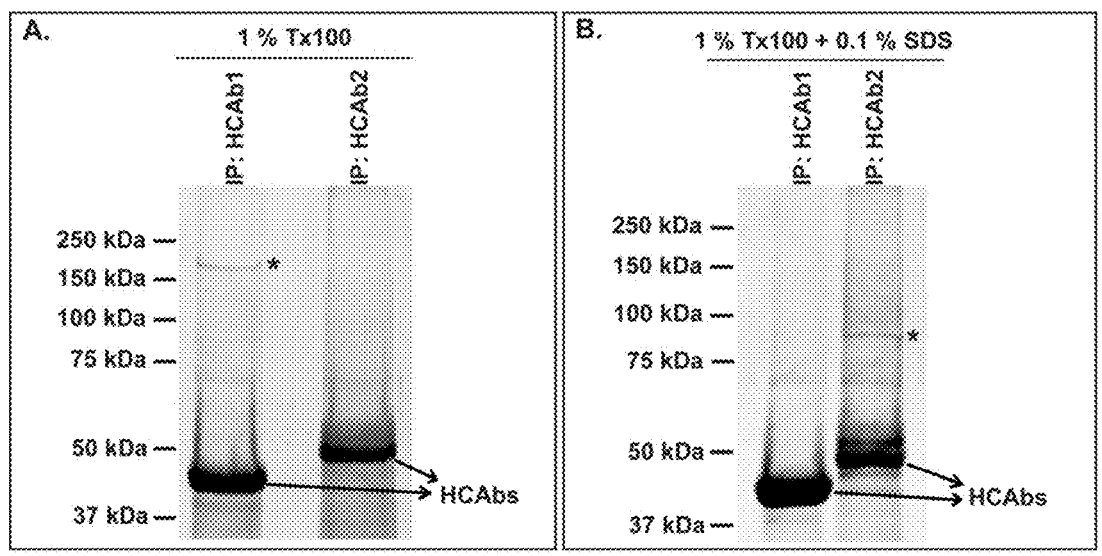
FIGURE 3 A and B

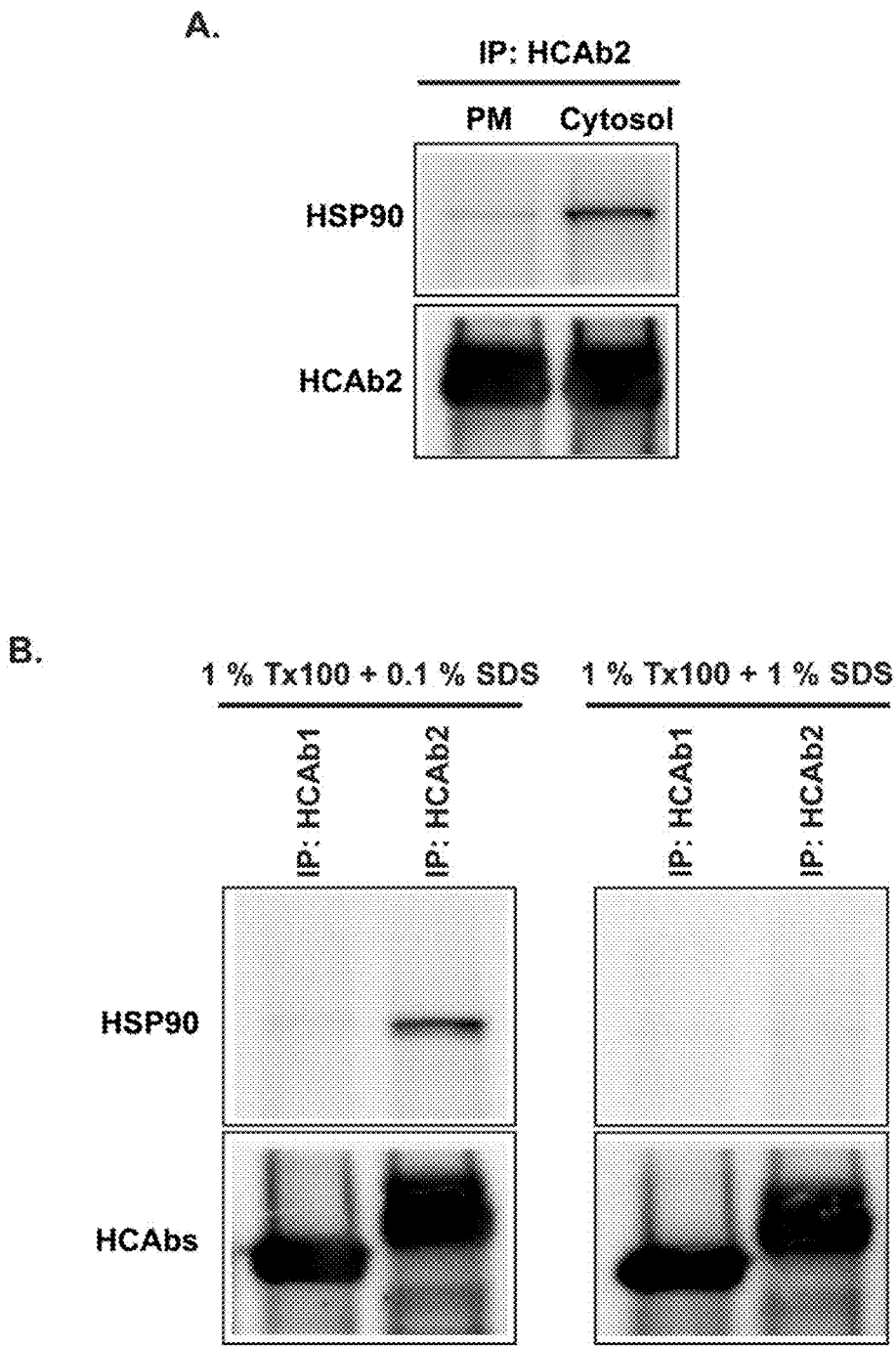
FIGURE 4 A and B

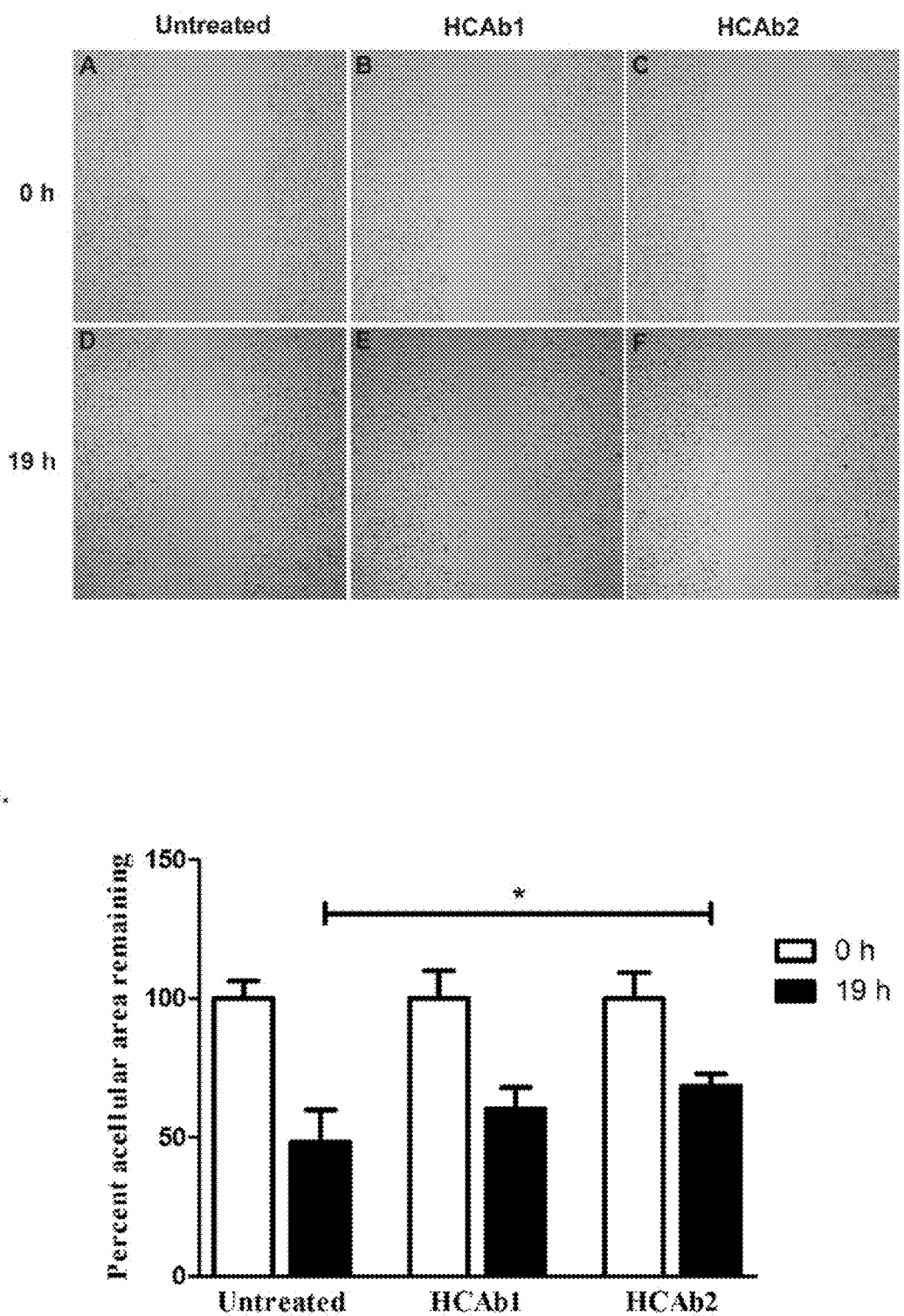
FIGURE 5 A-G

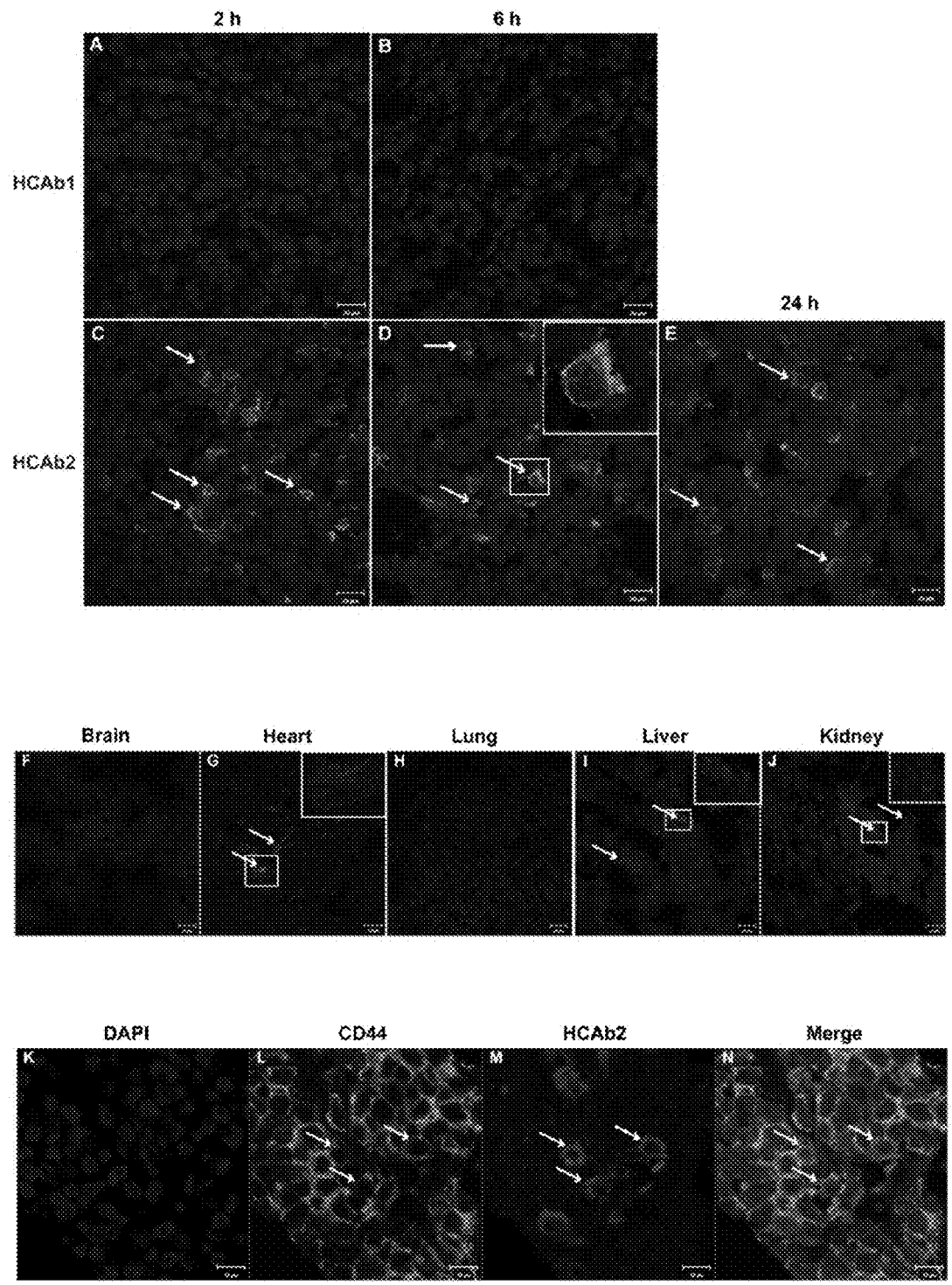
FIGURE 6 A-N

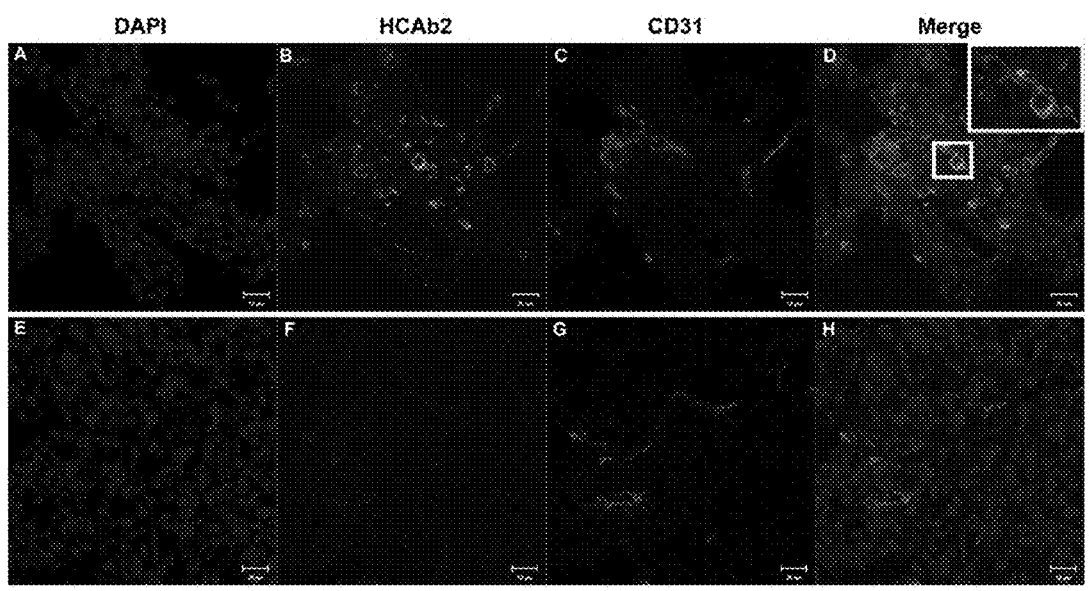
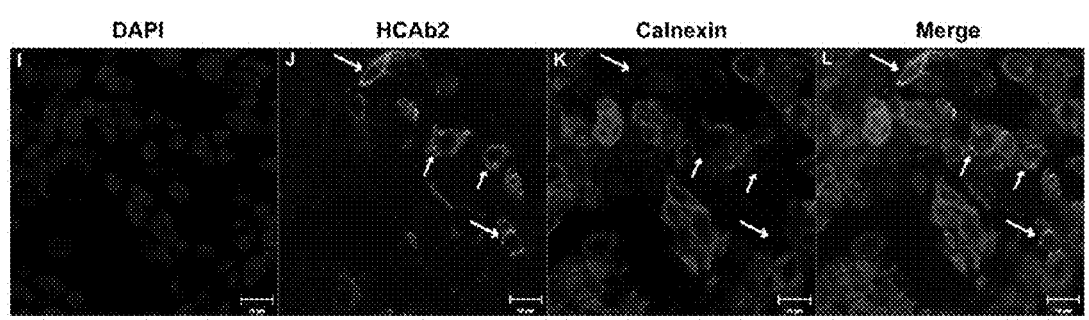
FIGURE 7 A-L

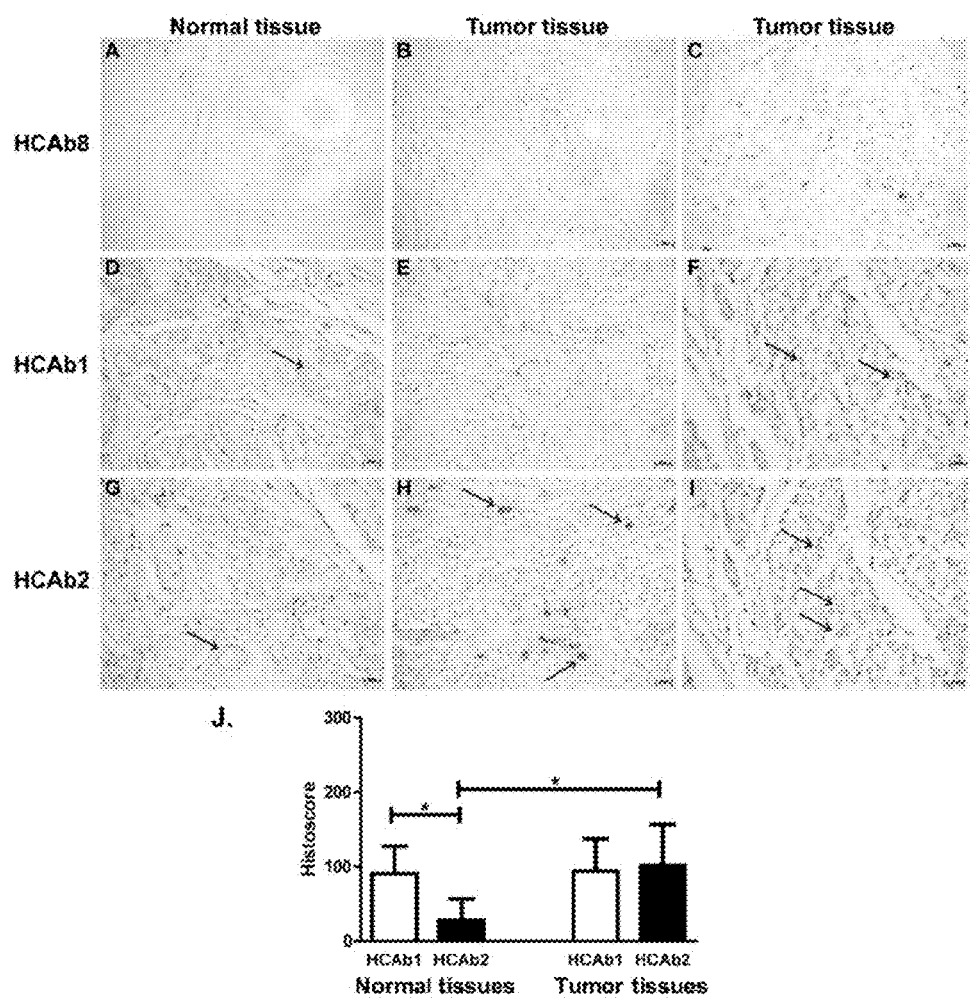
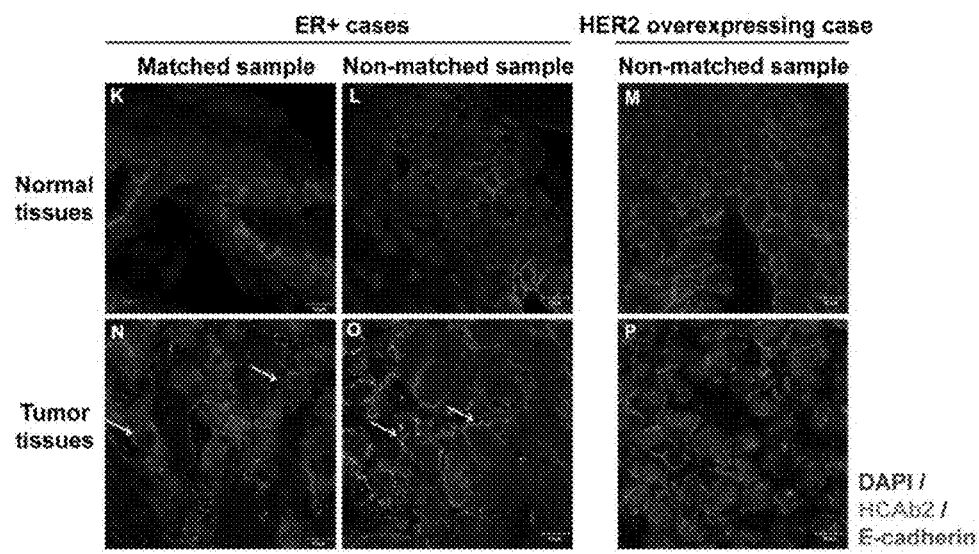
FIGURE 8 A-P

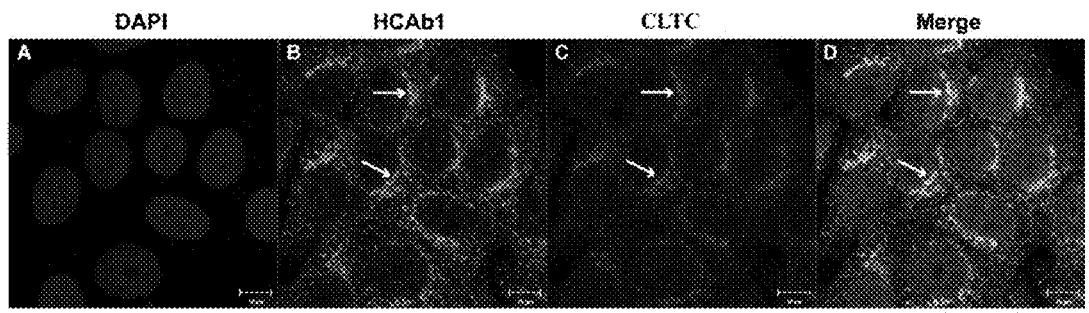
Figure 9A-D
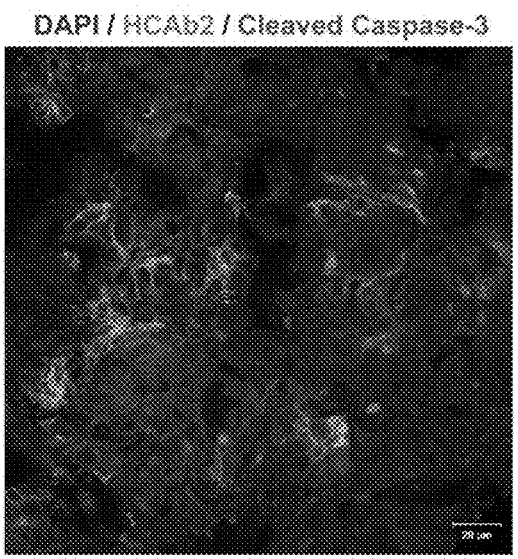
Figure 10

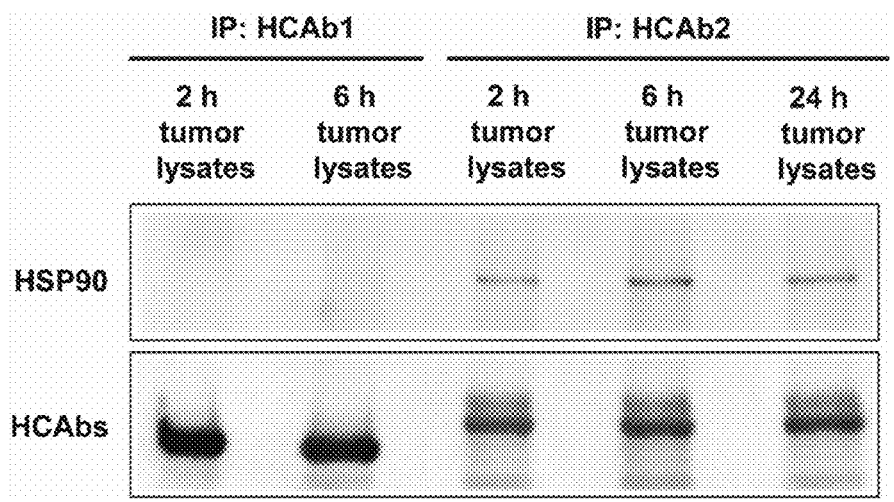
FIGURE 11
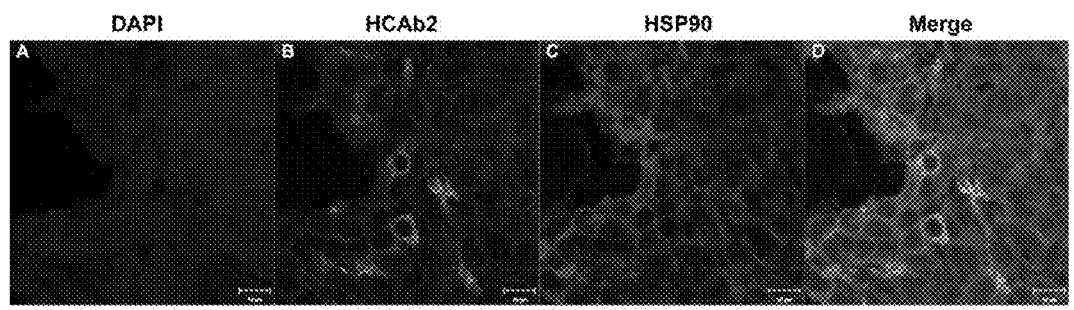
FIGURE 12A-D
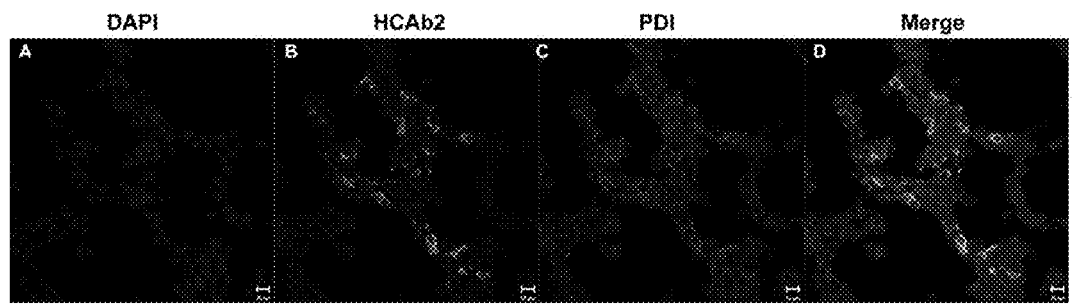
FIGURE 13A-D

```
LC1  MYRMQLLSCIALSLALXXNSQSVLTQPPSSSGTPGQ---RVTISCSGSSSNIGSN-TVNWY
LC3  MYRMQLLSCIALSLALVTNSQSVLTQPPSASGTPGQ---SVTISCSGSTSTIGSNY-VFWY
LC5  MYRMQLLSCIALSLALVTNSQSVLTQPPSVSGAPGQ---RVTISCTGSSSNIGADYDVHWY
LC6  MYRMQLLSCIALSLALVTNSQSVLTQPPSVSGAPGQ---RVTISCTGSSSNIGAGYDVQWY

LC1  QQLPGTAPKLLIYDNSNRPSGVPDRFSGSKSGTSASLAISGLRSEDEADYYCAAWDDSLN
LC3  RQLPGTAPKLLVYDNTNRPSGVPDRFSGSKSGTSASLAISGLRSEDEADYYCAAWDDSL-
LC5  QQLPGTAPKLLIYDNTNRPSGVPDRFSGSKSGTSASLAITGLQTEDEADYYCQSYDGSL-
LC6  QQLPGTAPKLLIYGNSWPSGVPDRFSGSKSGTSASLAITGLQAEDEAVYHCQTYDSSL-

LC1  GHWVFGGGTQLTVLSVLGQPKAAPSVTLFPPSSEELQANKATLVCLISDFYPGAVTVAWK
LC3  SGRVFGGGTQLTVLSVLGQPKAAPSVTLFPPSSEELQANKATLVCLISDFYPGAVTVAWK
LC5  GEGVFGGGTQLTVLSVLGQPKAAPSVTLFPPSSEELQANKATLVCLISDFYPGAVTVAWK
LC6  SGSVFGGGTRLTVLSVLGQPKAAPSVTLFPPSSEELQANKATLVCLISDFYPGAVTVAWK

LC1  ADSSPVKAGVETTTPSKXSNNKYAASXYLSLTPEQXKSHRKLQLPRSRMKGAPWKRQWPP
LC3  ADSSPVKAGVETTTPSKQSNNKYAASSYLSLTPEQWKSHRSYSCQV-THEGSTVEKTVAP
LC5  ADSSPVKAGVETTTPSKQSNNKYAASSYLSLTPEQWKSHRSYSCQV-THEGSTVEKTVAP
LC6  ADSSPVKAGVETTTPSKQSNNKYAASSYLSLTPEQWKSHRSYSCQV-THEGSTVEKTVAP

LC1  TECS
LC3  TECS
LC5  TECS
LC6  TECS
```

LC1= SEQ ID NO: 5

LC3= SEQ ID NO: 6

LC5= SEQ ID NO: 7

LC6= SEQ ID NO: 8

FIGURE 14

SEQUENCE LISTING

<160> NUMBER OF SEQ ID NOS: 12

<210> SEQ ID NO 1
<211> LENGTH: 8
<212> TYPE: PRT
<213> ORGANISM: Artificial Sequence
<220> FEATURE:
<223> OTHER INFORMATION: complementary determining region

<400> SEQUENCE: 1

Gly Tyr Arg Leu Ser Glu Leu Ser
1               5

<210> SEQ ID NO 2
<211> LENGTH: 8
<212> TYPE: PRT
<213> ORGANISM: Artificial Sequence
<220> FEATURE:
<223> OTHER INFORMATION: complementary determining region

<400> SEQUENCE: 2

Ile Ser Gly Trp Asp Gly Asn Thr
1               5

<210> SEQ ID NO 3
<211> LENGTH: 8
<212> TYPE: PRT
<213> ORGANISM: Artificial Sequence
<220> FEATURE:
<223> OTHER INFORMATION: complementary determining region

<400> SEQUENCE: 3

Ala Arg Ala Ser Gly Tyr Asn Tyr
1               5

<210> SEQ ID NO 4
<211> LENGTH: 122
<212> TYPE: PRT
<213> ORGANISM: Homo sapiens

<400> SEQUENCE: 4

Gln Val Gln Leu Val Gln Ser Gly Ala Glu Val Lys Lys Pro Gly Ala
1               5                   10                  15

Ser Val Arg Val Ser Cys Lys Ile Phe Gly Tyr Arg Leu Ser Glu Leu
            20                  25                  30

Ser Ile His Trp Val Arg Gln Ala Pro Gly Lys Gly Leu Glu Trp Met
        35                  40                  45

Gly Trp Ile Ser Gly Trp Asp Gly Asn Thr Thr Tyr Thr Gln Asn Leu
    50                  55                  60

Gln Gly Arg Val Thr Met Thr Thr Asp Thr Ser Thr Asn Ser Ala Tyr
65                  70                  75                  80

Met Glu Leu Arg Ser Leu Arg Ser Asp Asp Thr Ala Val Tyr Tyr Cys
                85                  90                  95

Ala Arg Ala Ser Gly Tyr Asn Tyr Ser Tyr Arg Pro Leu Asp Phe Trp
            100                 105                 110

Gly Arg Gly Thr Leu Val Thr Val Ser Ser
        115                 120

<210> SEQ ID NO 5
<211> LENGTH: 241
<212> TYPE: PRT
<213> ORGANISM: Artificial Sequence
<220> FEATURE:

<223> OTHER INFORMATION: light chain sequence
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (195)..(195)
<223> OTHER INFORMATION: Xaa can be any naturally occurring amino acid
<220> FEATURE:
<221> NAME/KEY: misc_feature
<222> LOCATION: (204)..(204)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid

<400> SEQUENCE: 5

Met Tyr Arg Met Gln Leu Leu Ser Cys Ile Ala Leu Ser Leu Ala Leu
1               5                   10                  15

Xaa Xaa Asn Ser Gln Ser Val Leu Thr Gln Pro Pro Ser Ser Ser Gly
                20                  25                  30

Thr Pro Gly Gln Arg Val Thr Ile Ser Cys Ser Gly Ser Ser Ser Asn
        35                  40                  45

Ile Gly Ser Asn Thr Val Asn Trp Tyr Gln Gln Leu Pro Gly Thr Ala
    50                  55                  60

Pro Lys Leu Leu Ile Tyr Asp Asn Ser Asn Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Arg Ser Glu Asp Glu Ala Asp Tyr Tyr Cys Ala Ala Trp
            100                 105                 110

Asp Asp Ser Leu Asn Gly His Trp Val Phe Gly Gly Gly Thr Gln Leu
        115                 120                 125

Thr Val Leu Ser Val Leu Gly Gln Pro Lys Ala Ala Pro Ser Val Thr
    130                 135                 140

Leu Phe Pro Pro Ser Ser Glu Glu Leu Gln Ala Asn Lys Ala Thr Leu
145                 150                 155                 160

Val Cys Leu Ile Ser Asp Phe Tyr Pro Gly Ala Val Thr Val Ala Trp
                165                 170                 175

Lys Ala Asp Ser Ser Pro Val Lys Ala Gly Val Glu Thr Thr Thr Pro
            180                 185                 190

Ser Lys Xaa Ser Asn Asn Lys Tyr Ala Ala Ser Xaa Tyr Leu Ser Leu
        195                 200                 205

Thr Pro Glu Gln Xaa Lys Ser His Arg Lys Leu Gln Leu Pro Arg Ser
    210                 215                 220

Arg Met Lys Gly Ala Pro Trp Lys Arg Gln Trp Pro Pro Thr Glu Cys
225                 230                 235                 240

Ser

<210> SEQ ID NO 6
<211> LENGTH: 239
<212> TYPE: PRT
<213> ORGANISM: Artificial Sequence
<220> FEATURE:
<223> OTHER INFORMATION: light chain sequence

<400> SEQUENCE: 6

Met Tyr Arg Met Gln Leu Leu Ser Cys Ile Ala Leu Ser Leu Ala Leu
1               5                   10                  15

Val Thr Asn Ser Gln Ser Val Leu Thr Gln Pro Ser Ala Ser Gly
            20                  25                  30

Thr Pro Gly Gln Ser Val Thr Ile Ser Cys Ser Gly Ser Thr Ser Thr
        35                  40                  45

Ile Gly Ser Asn Tyr Val Phe Trp Tyr Arg Gln Leu Pro Gly Thr Ala
50                  55                  60

Pro Lys Leu Leu Val Tyr Asp Asn Thr Asn Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Arg Ser Glu Asp Glu Ala Asp Tyr Tyr Cys Ala Ala Trp
            100                 105                 110

Asp Asp Ser Leu Ser Gly Arg Val Phe Gly Gly Gly Thr Gln Leu Thr
                115                 120                 125

Val Leu Ser Val Leu Gly Gln Pro Lys Ala Ala Pro Ser Val Thr Leu
130                 135                 140

Phe Pro Pro Ser Ser Glu Glu Leu Gln Ala Asn Lys Ala Thr Leu Val
145                 150                 155                 160

Cys Leu Ile Ser Asp Phe Tyr Pro Gly Ala Val Thr Val Ala Trp Lys
                165                 170                 175

Ala Asp Ser Ser Pro Val Lys Ala Gly Val Glu Thr Thr Thr Pro Ser
            180                 185                 190

Lys Gln Ser Asn Asn Lys Tyr Ala Ala Ser Ser Tyr Leu Ser Leu Thr
                195                 200                 205

Pro Glu Gln Trp Lys Ser His Arg Ser Tyr Ser Cys Gln Val Thr His
            210                 215                 220

Glu Gly Ser Thr Val Glu Lys Thr Val Ala Pro Thr Glu Cys Ser
225                 230                 235

<210> SEQ ID NO 7
<211> LENGTH: 240
<212> TYPE: PRT
<213> ORGANISM: Artificial Sequence
<220> FEATURE:
<223> OTHER INFORMATION: light chain sequence

<400> SEQUENCE: 7

Met Tyr Arg Met Gln Leu Leu Ser Cys Ile Ala Leu Ser Leu Ala Leu
1               5                   10                  15

Val Thr Asn Ser Gln Ser Val Leu Thr Gln Pro Pro Ser Val Ser Gly
            20                  25                  30

Ala Pro Gly Gln Arg Val Thr Ile Ser Cys Thr Gly Ser Ser Ser Asn
        35                  40                  45

Ile Gly Ala Asp Tyr Asp Val His Trp Tyr Gln Gln Leu Pro Gly Thr
50                  55                  60

Ala Pro Lys Leu Leu Ile Tyr Asp Asn Thr Asn Arg Pro Ser Gly Val
65                  70                  75                  80

Pro Asp Arg Phe Ser Gly Ser Lys Ser Gly Thr Ser Ala Ser Leu Ala
                85                  90                  95

Ile Thr Gly Leu Gln Thr Glu Asp Glu Ala Asp Tyr Tyr Cys Gln Ser
            100                 105                 110

Tyr Asp Gly Ser Leu Gly Glu Gly Val Phe Gly Gly Gly Thr Gln Leu
                115                 120                 125

Thr Val Leu Ser Val Leu Gly Gln Pro Lys Ala Ala Pro Ser Val Thr
130                 135                 140

```
Leu Phe Pro Pro Ser Ser Glu Glu Leu Gln Ala Asn Lys Ala Thr Leu
145                 150                 155                 160

Val Cys Leu Ile Ser Asp Phe Tyr Pro Gly Ala Val Thr Val Ala Trp
                165                 170                 175

Lys Ala Asp Ser Ser Pro Val Lys Ala Gly Val Glu Thr Thr Thr Pro
            180                 185                 190

Ser Lys Gln Ser Asn Asn Lys Tyr Ala Ala Ser Ser Tyr Leu Ser Leu
        195                 200                 205

Thr Pro Glu Gln Trp Lys Ser His Arg Ser Tyr Ser Cys Gln Val Thr
    210                 215                 220

His Glu Gly Ser Thr Val Glu Lys Thr Val Ala Pro Thr Glu Cys Ser
225                 230                 235                 240

<210> SEQ ID NO 8
<211> LENGTH: 240
<212> TYPE: PRT
<213> ORGANISM: Artificial Sequence
<220> FEATURE:
<223> OTHER INFORMATION: light chain sequence

<400> SEQUENCE: 8

Met Tyr Arg Met Gln Leu Leu Ser Cys Ile Ala Leu Ser Leu Ala Leu
1               5                   10                  15

Val Thr Asn Ser Gln Ser Val Leu Thr Gln Pro Pro Ser Val Ser Gly
                20                  25                  30

Ala Pro Gly Gln Arg Val Thr Ile Ser Cys Thr Gly Ser Ser Ser Asn
            35                  40                  45

Ile Gly Ala Gly Tyr Asp Val Gln Trp Tyr Gln Gln Leu Pro Gly Thr
        50                  55                  60

Ala Pro Lys Leu Leu Ile Tyr Gly Asn Ser Asn Trp Pro Ser Gly Val
65                  70                  75                  80

Pro Asp Arg Phe Ser Gly Ser Lys Ser Gly Thr Ser Ala Ser Leu Ala
                85                  90                  95

Ile Thr Gly Leu Gln Ala Glu Asp Glu Ala Val Tyr His Cys Gln Thr
            100                 105                 110

Tyr Asp Ser Ser Leu Ser Gly Ser Val Phe Gly Gly Gly Thr Lys Leu
        115                 120                 125

Thr Val Leu Ser Val Leu Gly Gln Pro Lys Ala Ala Pro Ser Val Thr
130                 135                 140

Leu Phe Pro Pro Ser Ser Glu Glu Leu Gln Ala Asn Lys Ala Thr Leu
145                 150                 155                 160

Val Cys Leu Ile Ser Asp Phe Tyr Pro Gly Ala Val Thr Val Ala Trp
                165                 170                 175

Lys Ala Asp Ser Ser Pro Val Lys Ala Gly Val Glu Thr Thr Thr Pro
            180                 185                 190

Ser Lys Gln Ser Asn Asn Lys Tyr Ala Ala Ser Ser Tyr Leu Ser Leu
        195                 200                 205

Thr Pro Glu Gln Trp Lys Ser His Arg Ser Tyr Ser Cys Gln Val Thr
    210                 215                 220

His Glu Gly Ser Thr Val Glu Lys Thr Val Ala Pro Thr Glu Cys Ser
225                 230                 235                 240
```

```
<210> SEQ ID NO 9
<211> LENGTH: 39
<212> TYPE: DNA
<213> ORGANISM: Artificial Sequence
<220> FEATURE:
<223> OTHER INFORMATION: primer

<400> SEQUENCE: 9
ttcggcgatc gccatgcagg tgcagctggt gsagtctgg                                    39

<210> SEQ ID NO 10
<211> LENGTH: 48
<212> TYPE: DNA
<213> ORGANISM: Artificial Sequence
<220> FEATURE:
<223> OTHER INFORMATION: primer

<400> SEQUENCE: 10
gccttggaag tacaggttct caccggtacg cgtagaatcg agaccgag                          48

<210> SEQ ID NO 11
<211> LENGTH: 42
<212> TYPE: DNA
<213> ORGANISM: Artificial Sequence
<220> FEATURE:
<223> OTHER INFORMATION: primer

<400> SEQUENCE: 11
tgggctcgag gccttggaag tacaggttct caccggtacg cg                                42

<210> SEQ ID NO 12
<211> LENGTH: 120
<212> TYPE: PRT
<213> ORGANISM: Homo sapiens

<400> SEQUENCE: 12

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Glu Gly Gln Trp Leu Val Gln Ile Asp Tyr Trp Gly Gln
            100                 105                 110

Gly Thr Leu Val Thr Val Ser Ser
        115                 120
```

ANTIBODY AND ANTIGEN-BINDING FRAGMENT COMPOSITIONS TARGETING CELL SURFACE ANTIGENS IN TUMORS AND METHODS OF USE THEREOF

CROSS-REFERENCE TO RELATED APPLICATIONS

This application claims priority to U.S. Provisional Application 62/356,813 filed on Jun. 30, 2016, which is incorporated herein by reference in its entirety.

STATEMENT REGARDING FEDERALLY SPONSORED RESEARCH & DEVELOPMENT

This invention was made with government support under grant CA143531 awarded by the National Institutes of Health and grant W81XWH-11-1-0440 awarded by the United States Army Medical Research and Materiel Command. The government has certain rights in the invention

FIELD OF THE DISCLOSURE

The disclosure contained herein is in the general field of therapeutics for cancer, and more specifically, therapeutics based on antibodies that target surface membrane components of tumor cells.

BACKGROUND

Antibodies against various tumor associated antigens have been widely used in the treatment of different tumors. The emergence of Cetuximab, Trastuzumab and Ipilimumab against solid tumors as well as Rituximab and Ofatumubab against hematological malignancies has highlighted the significant role of antibodies in effective cancer therapy. Trastuzumab and Pertuzumab, which target human epidermal growth factor receptor 2 (HER2) have been shown to synergistically inihibit the growth of HER2 over-expressing breast cancer cells and also kill them. These examples highlight the importance of antibodies in the treatment of tumors as well as the need for identifying more tumor specifc antibodies.

In order to develop tumor specific antibodies, the identity of the target antigens has to be known. Previously described examples of tumor specific antibodies were developed by understanding the basic aspects of tumor biology. For instance, breast tumors that over-express HER2 receptor rely on this signaling pathway for survival and proliferation. Therefore, anti-HER2 receptor antibodies such as Trastuzumab and Pertuzumab were developed to specifically target HER2 over-expressing tumors. Although successful, this targeted approach is limited by our current understanding of tumor biology and does not lead to identification of novel tumor associated antigens.

Humoral immune responses against tumor antigens have been observed in various cancer patients as evidenced by serum antibodies as well as activated B-cells within the sentinel lymph nodes. In previous studies, a unique strategy was developed to identify novel tumor associated antigens. The strategy involved identification of activated and proliferating B-cells within the sentinel lymph nodes of breast cancer patients. Without being held to theory, it was hypothesized that these B-cells could be activated by unique antigens derived from the tumor. Therefore, analyzing antibodies produced by these B-cells could lead to the identification of tumor associated antigens. Previously, cDNA molecules of variable heavy chain domains were generated from the activated B-cells. cDNA molecules that were part of clonal groups as well as exhibited somatic hypermutation within the complementarity determining regions were selected and sequenced. In the indexed study, single domain antibodies from the activated B-cells were synthesized and screened to identify tumor associated antigens. Using this approach, neuroplastin was identified to be a breast tumor associated antigen that was expressed at high levels in 20% of invasive breast tumors and 50% of those that became metastatic to distal sites. Identification of neuroplastin using these single domain antibodies validated the power of this research strategy to identify novel tumor antigens.

What is needed are additional therapeutic antibodies for the treatment of cancers including late-stage disseminating cancers.

BRIEF SUMMARY

In one aspect, an isolated antibody or antigen-binding fragment comprises a heavy chain variable region comprising three heavy chain complementary determining regions (HCDRs), wherein the sequence of HCDR1 is GYRLSELS (SEQ ID NO: 1), the sequence of HCDR2 is ISGWDGNT (SEQ ID NO: 2), and the sequence of HCDR3 is ARASGYNY (SEQ ID NO: 3), wherein the isolated antibody or antigen-binding fragment specifically binds human HSP90, specifically HSP90 beta.

In another aspect, a method of detecting the presence of HSP90, specifically HSP90 beta, in a biological sample comprises contacting the biological sample with the foregoing isolated antibody or antigen-binding fragment and detecting binding of the isolated antibody or antigen-binding fragment to HSP90, specifically HSP90 beta, wherein binding indicates the presence of HSP90, specifically, HSP90 beta in the sample.

In another aspect, a method of treating a human subject in need of treatment for cancer comprises administering to the human subject the foregoing isolated antibody or antigen-binding fragment.

Also included are pharmaceutical compositions comprising the isolated antibody or antigen-binding fragment and a pharmaceutically acceptable carrier.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-O show that HCAb2 preferentially bound to the surface of MDA-MB-231 cells. FIG. 1 A shows an alignment of the amino acid sequences of HCAb1 and HCAb2 revealing the mutations (*) in comparison to their respective germline VDJ sequences. HCAb1 and HCAb2 nucleotide sequences were analyzed using IMGT/V-QUEST program to determine the VDJ gene segments of both the antibodies as well as the mutations in the CDR and FR domains. FIG. 1 B is an immunoblot depicting differences in the monomeric molecular weights of 8 different heavy chain antibodies. Purified heavy chain antibodies (300 ng) were run on a reducing SDS-PAGE gel, transferred onto a nitrocellulose membrane and detected using anti-mouse IgG antibody. FIG. 1 C shows flow cytometry screening of HCAb1 and HCAb2 using MCF10A, MCF7 and MDA-MB-231 cells. HCAb1 (green peak), HCAb2 (yellow peak), isotype control (red peak) and unstained (blue peak). FIGS. 1 D-O show an immunofluorescence analysis of HCAb1 and HCAb2 on HMEC, MCF7 and MDA-MB-231 cells. (FIG. 1D-I) show non-permeabilized cells stained with HCAb1 (FIG. 1 D-F) and HCAb2 (FIG. 1 G-I) to determine cell surface staining. (FIG. 1 J-O) Permeabilized cells were stained with HCAb1 (FIG. 1 J-L) and HCAb2 (FIG. 1 M-O) to determine intracellular staining. Scale bar represents 10 μm.

FIGS. 2A-R show that HCAb2 bound strongly to primary breast tumor tissues in comparison to normal breast tissues. FIG. 2 A-H show immunofluorescence analysis of HCAb2 on primary breast normal and ER+tumor tissues. Methanol:acetone fixed normal (A-D) and ER+tumor tissues (E-H) were stained with HCAb2 and E-cadherin (epithelial marker). Matched samples represent the normal and tumor tissues derived from the same patient. Arrows indicate cells with positive HCAb2 staining on the cell surface. FIG. 2 I-L show an immunofluorescence analysis of HCAb2 on ER+tumor tissues. ER+tumor tissues were stained with HCAb2 and E-cadherin. HCAb2 showed positive staining of E-cadherin negative tumor cells. Panel J is the magnified view of the inset shown in panel I. FIG. 2 M-R show an immunofluorescence analysis of HCAb2 on matched normal and triple negative tumor tissues. (FIG. 2 M-O) Normal tissues were stained with HCAb2 and E-cadherin, while the tumor tissues were stained with HCAb2 and N-cadherin. For all the samples nuclei were stained with DAPI and the scale bar represents 10 μm.

FIGS. 3 A and B show an identification of the target antigens of HCAb1 and HCAb2. FIGS. 3 A and B show immunoprecipitation of respective target antigens by HCAb1 and HCAb2. 20 μg of HCAb1 and HCAb2 were used to immunoprecipitate the target antigens from 1% Triton X-100 (A) or 1% Triton X-100+0.1% SDS (B) MDA-MB-231 lysates. The immunoprecipitated proteins were run on a reducing SDS-PAGE gel and the proteins in the gel were stained with SYPRO® Ruby stain. * indicates the specific band for HCAb1 (A) and HCAb2 (B).

FIGS. 4 A and B show a validation of the target antigens of HCAb1 and HCAb2. FIG. 4 A shows a validation of HSP90 to be the target antigen of HCAb2. Immunoprecipitation of HSP90 was performed from cytosolic and plasma membrane (PM) fractions using HCAb2. The immunoprecipitated HSP90 was detected using a commercial HSP90 antibody. FIG. 4B shows an immunoprecipitation of recombinant human HSP90β protein using HCAb1 and HCAb2. HCAb1 and HCAb2 (5 μg each) were used to immunoprecipitate recombinant HSP90β (1 μg) resuspended in either 1% Triton X-100+0.1% SDS or 1% Triton X-100+1% SDS buffers. The immunoprecipitated HSP90β protein was detected using a commercial HSP90 antibody. Equal amounts of HCAb1 and HCAb2 were pulled down as detected by anti-mouse IgG antibody.

FIGS. 5A-G show that HCAb2 reduced the migration of MDA-MB-231 cells in scratch assay. FIGS. 4 A-F are representative images of scratch assay, T=0 h (panels A-C) and T=19 h (panels D-F). Scratches were made using 200 μl pipet tips and T=0 h images were taken. Subsequently cells were left untreated or incubated with HCAb1 and HCAb2 (5 μg each) and imaged after 19 h. Scale bar represents 100 μm. FIG. 4G shows quantification of the percent acellular area remaining after 19 h of treatment with HCAb1 and HCAb2. Acellular area at T=0 h and T=19 h was determined for each well using Image-Pro software (n=4 wells per treatment). Average area at T=0 h for each treatment was set to be 100% and the areas at T=19 h were normalized to the corresponding average acellular area at T=0h. Percent acellular area remaining was calculated accordingly. Error bars represent standard deviation and statistical significance was determined by Student t test, *=p≤0.05.

FIGS. 6A-N show that HCAb2 localized specifically to MDA-MB-231 xenograft tumors in immunodeficient mice. FIGS. 6 A-E are representative images showing the localization of HCAb2 to the tumors at 2 h, 6 h and 24 h time points. Female NSG mice bearing tumors ranging from 300-500 mm$^3$ were retro-orbitally injected with 12 μg of HCAb1 (n=2) and HCAb2 (n=3) into respective animals. After 2 h, 6 h and 24 h mice were euthanized and tumors along with various normal tissues were stained to detect HCAb1 and HCAb2 localization. HCAb1 did not localize to the tumors (panels A and B), while HCAb2 localizes to the tumors at the earliest time point (panel C) as well as the later time points of 6 h (panel D) and 24 h (panel E). Arrows indicate cells with HCAb2 staining. Insets reveal magnified image, scale bar represents 20 μm. FIGS. 6 F-J show that HCAb2 was observed at low levels in some normal tissues. Frozen sections of brain (panel F), heart (panel G), lung (panel H), liver (panel I) and kidney (panel J) tissues from the 24 h time point mouse were analyzed to detect the presence of HCAb2. Low levels of HCAb2 were detected in the heart (panel G), liver (panel I) and kidney tissues (panel J). Arrows indicate HCAb2 localization. Insets reveal magnified image, scale bar represents 20 μm. FIGS. 6 K-N show an immunofluorescence analysis of CD44 staining and HCAb2 localization in the xenograft tumor. 24 h time point tumor section was stained to detect CD44+ cells as well as the localization of HCAb2. From panels L, M and N it can be observed that HCAb2 localizes to the MDA-MB-231 cells. Arrows indicate cells with reduced CD44 staining with HCAb2 signal. Scale bar represents 10 μm.

FIGS. 7 A-L show that HCAb2 specifically targeted a unique population of MDA-MB-231 cells in the xenograft tumors. FIGS. 7 A-H show an immunofluorescence analysis of CD31 staining and HCAb2 localization in the xenograft tumor. 24 h time point tumor section was incubated with anti-CD31 and Alexa Fluor® 488 anti-mouse IgG antibodies. Nuclei were stained with DAPI. Panels A-D reveal region with HCAb2 localization and positive CD31 staining. Panels E-H reveal region within the same tumor without HCAb2 localization but with positive CD31 staining. Scale bar represents 20 μm. FIGS. 7 I-L shows an immunofluorescence analysis showing lack of calnexin and HCAb2 localization in the xenograft tumor. 24 h time point tumor section was incubated with anti-calnexin and Alexa Fluor® 488 anti-mouse IgG antibodies. HCAb2 localized to MDA-MB-231 cells that lacked calnexin staining as seen from panels K-L. Scale bar represents 10 μm.

FIGS. 8 A-P show that HCAb2 showed preferential staining to primary breast tumor tissues in comparison to normal breast tissues. FIGS. 8 A-I show an immunohistochemical analysis of HCAbs on breast tissue microarrays. BR1009 breast tissue microarrays were stained with HCAb8 (negative control) (A-C), HCAb1 (D-F) and HCAb2 (G-I). Arrows indicate epithelial cells, scale bar represents 20 μm. FIG. 8J shows quantification of the immunohistochemical staining using histoscores. Tissue sections stained with the HCAbs were visually evaluated and given staining intensity scores ranging from 0-3 as well as percent positivity for each intensity score was noted to obtain the histoscores for each tissue. Error bars represent SD and statistical significance was determined by Student t test, * p<0.05. FIGS. 8 K-P show an immunofluorescence analysis of HCAb2 on primary breast normal and tumor tissues. Human primary breast normal and tumor frozen sections were stained with HCAb2 and E-cadherin. (K, N) represent matched normal and ER+tumor tissues, while (L, O) represent non-matched normal and ER+tumor tissues. (M, P) represent non-matched normal and HER2 overexpressing tumor tissues. Arrows indicate cells with positive HCAb2 staining on the cell surface. Nuclei were stained with DAPI and the scale bar represents 10 μm.

FIGS. 9A-D show that clathrin heavy chain protein is the target antigen of HCAb1. FIGS. 9 A-D show MCF7 cells that were incubated with HCAb1 and commercial clathrin heavy chain antibody. Arrows indicate the regions that show co-localization of HCAb1 and CLTC antibody. Nuclei were stained with DAPI. Scale bar represents 10 μm.

FIG. 10 shows that HCAb2 internalization did not target apoptotic xenograft tumor cells. 24 h time point tumor section was incubated with anti-cleaved Caspase-3 and Alexa Fluor® 488 anti-mouse IgG antibodies. HCAb2 did not show localization to cells that were positive for cleaved Caspase-3 staining. Scale bar represents 20 μm.

FIG. 11 shows immunoprecipitation of HSP90 from xenograft tumor lysates using HCAb2. RIPA lysates of xenograft tumor pieces were used for immunoprecipitation with 15 μg of HCAb1 and HCAb2. Immunoprecipitated HSP90β protein was detected on an immunoblot using commercial HSP90 antibody. HCAb2 pulled down HSP90β from 2 h, 6 h and 24 h tumor lysates while HCAb1 did not pull down HSP90β. Equal amounts of HCAb1 and HCAb2 were pulled down as detected by anti-mouse IgG antibody.

FIGS. 12A-D show that HCAb2 localized xenograft tumor cells did not show variations in the levels of intracellular HSP90. FIGS. 12 A-D show 24 h time point tumor section was incubated with anti-HSP90 and Alexa Fluor® 488 anti-mouse IgG antibodies. Isolated HCAb2 localization was observed (panel B) while uniform HSP90 staining was observed (panel C) throughout the tumor section. Scale bar represents 20 μm.

FIGS. 13A-D show that HCAb2 localized xenograft tumor cells express protein disulfide isomerase. FIGS. 13 A-D show 24h time point tumor section was incubated with anti-PDI and Alexa Fluor® 488 anti-mouse IgG antibodies. Uniform PDI staining was observed in all the cells (panel C) throughout the tumor section. Scale bar represents 10 μm.

FIG. 14 shows a sequence alignment of the light chains of SEQ IS NOS. 5-8 (LC1, LC3, LC5 and LC6, respectively).

The above-described and other features will be appreciated and understood by those skilled in the art from the following detailed description, drawings, and appended claims.

DETAILED DESCRIPTION

Monoclonal antibodies have been used to effectively treat various tumors. The inventors previously established a unique strategy to identify tumor specific antibodies by utilizing the B-cell response against breast tumor antigens in patient-derived sentinel lymph nodes. This approach led to the identification of a tumor specific single domain antibody that targeted neuroplastin. A sentinel lymph node derived heavy chain antibody (HCAb2) that targets cell surface HSP90β antigen on breast tumor cells but not normal cells was identified and characterized.

The inventors screened eight unique selected heavy chain antibodies (HCAbs) (HCAb1-8) and identified HCAb2 to show preferential cell surface staining on breast cancer cell lines. HCAb2 binds to primary breast tumor tissues and not to normal tissues. The inventors identified and validated that HCAb2 bound to cell surface HSP90 and also reduced migration of MDA-MB-231 cells in a scratch assay, consistent with HSP90 literature. In addition, the inventors showed that HCAb2 targets xenograft tumor cells in an in vivo mouse model, thus defining a potentially useful anti-tumor antibody.

Single domain antibodies are small (12-15 kDa) molecules that can bind to antigens with similar affinity as intact antibodies. While useful for their intended purpose, single domain antibodies lack the Fc region and thereby do not readily mediate effector functions such as antibody-dependent cell-mediated cytotoxicity and complement-dependent cytotoxicity. Also due to their small size, single domain antibodies can have a rather short serum half-life thereby reducing their in vivo tumor targeting efficacy. In order to circumvent these problems, single domain heavy chain cDNAs can be subcloned into a mammalian expression vector and to generate antibodies made up of variable heavy chain regions fused to the mouse Fc domain (HCAbs).

Flow cytometry screen identified HCAb2 to selectively bind to the surface of MDA-MB-231 cells in comparison to MCF10A and MCF7 cells. HCAb2 revealed punctate staining on MDA-MB-231 cells and also preferentially bound to human breast tumor tissues in comparison to normal breast tissues. The target antigen for HCAb2 was validated to be HSP90. HCAb2 also selectively targeted MDA-MB-231 xenograft tumor cells in vivo with little targeting to normal mouse tissues. Finally, HCAb2 specifically targeted calnexin negative cells within the xenograft tumors.

HCAb2 was thus identified as a breast tumor specific heavy chain antibody targeting cell surface HSP90β. HCAb2 showed positive binding to both E-cadherin positive and negative tumor cells in primary human tissues. HCAb2 also targeted MDA-MB-231 xenograft tumor cells in vivo suggesting that HCAb2 could be an ideal tumor targeting antibody.

The term "whole antibody" includes immunoglobulin molecules comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2, and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term "monoclonal antibody" refers to a preparation of antibody molecules of single molecular composition. A monoclonal antibody composition displays a single binding specificity and affinity for a particular epitope.

The term "single domain antibody" includes VHH, VH, and NAR V antibodies. VHH antibodies are single domain antibodies that are the variable region of a heavy chain of an antibody from camelid animals. VH antibodies are human heavy chain variable domains. NAR V antibodies are shark heavy chain variable regions. Preferred single domain antibodies are VH antibodies.

An antigen-binding "antibody fragment" comprises a portion of a full length antibody, preferably a variable domain thereof, or at least the antigen binding site thereof.

An "isolated" antibody is one which has been identified and separated or recovered from a component of its natural environment. Contaminant components of its natural environment are materials which would interfere with research, diagnostic or therapeutic uses for the antibody, and may include enzymes, hormones, and other proteinaceous or nonproteinaceous solutes. An "isolated antibody," as used herein, is also intended to refer to an antibody that is substantially free of other antibodies having different antigenic specificities.

As used herein, "specific binding" refers to antibody binding to a predetermined antigen. Typically, the antibody binds with an affinity of at least about $1\times10^{-7}$, specifically at least about $1\times10^{-8}$, and more specifically at least about $1\times10^{-9}$.

"Complementarity-determining region" or "CDR" refers to one of three hypervariable regions within the variable region of the heavy chain or the variable region of the light chain of an antibody molecule that form the N-terminal antigen-binding surface that is complementary to the three-dimensional structure of the bound antigen. Proceeding from the N-terminus of a heavy or light chain, these complementarity-determining regions are denoted as "CDR1," "CDR2," and "CDR3," respectively. CDRs are involved in antigen-antibody binding, and the CDR3 comprises a unique region specific for antigen-antibody binding. An antigen-binding site, therefore, may include six CDRs, comprising the CDR regions from each of a heavy and a light chain V region.

As used herein, "conservative substitutions" refers to modifications of a polypeptide that involve the substitution of one or more amino acids for amino acids having similar biochemical properties that do not result in loss of a biological or biochemical function of the polypeptide. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). The antibodies described herein may have conservative amino acid substitutions and still retain activity.

For nucleic acids and polypeptides, the term "substantial homology" indicates that two nucleic acids or two polypeptides, or designated sequences thereof, when optimally aligned and compared, are identical, with appropriate nucleotide or amino acid insertions or deletions, in at least about 80% of the nucleotides or amino acids, usually at least about 85%, preferably about 90%, 91%, 92%, 93%, 94%, or 95%, more preferably at least about 96%, 97%, 98%, 99%, 99.1%, 99.2%, 99.3%, 99.4%, or 99.5% of the nucleotides or amino acids. Alternatively, substantial homology for nucleic acids exists when the segments will hybridize under selective hybridization conditions to the complement of the strand. Nucleic acid sequences and polypeptide sequences may have substantial homology to the specific nucleic acid sequences and amino acid sequences recited herein.

The antibodies described herein include antibodies having "conservative sequence modifications", nucleotide and amino acid sequence modifications which do not affect or alter the above-mentioned characteristics of the antibody.

Preferred antibodies, including single chain antibodies, specifically bind Heat Shock Protein 90 (HSP90), specifically HSP90 beta, such as human HSP90 beta expressed on the surface of cancer cells.

In an embodiment, isolated antibody or antigen-binding fragment comprises a heavy chain variable region comprising three heavy chain complementary determining regions (HCDRs), wherein the sequence of HCDR1 is GYRLSELS (SEQ ID NO: 1), the sequence of HCDR2 is ISGWDGNT (SEQ ID NO: 2), and the sequence of HCDR3 is ARASGYNY (SEQ ID NO: 3), wherein the isolated antibody or antigen-binding fragment specifically binds human HSP90, specifically HSP90 beta. In an embodiment, the isolated antibody or antigen-binding fragment comprises a heavy chain region having at least 95% sequence identity SEQ ID NO: 4. In an embodiment, the isolated antibody or antigen-binding fragment comprises a heavy chain region of SEQ ID NO: 4.

```
                                            (SEQ ID NO: 4)
QVQLVQSGAEVKKPGASVRVSCKIFGYRLSELSIHWVRQAPGKGLEWMGWI
SGWDGNTTYTQNLQGRVTMTTDTSTNSAYMELRSLRSDDTAVYYCARASG
YNYSYRPLDFWGRGTLVTVSS
```

In an embodiment, the isolated antibody or antigen-binding fragment is a single chain antibody containing consisting of three heavy chain complementary determining regions (HCDRs), wherein the sequence of HCDR1 is GYRLSELS (SEQ ID NO: 1), the sequence of HCDR2 is ISGWDGNT (SEQ ID NO: 2), and the sequence of HCDR3 is ARASGYNY(SEQ ID NO: 3). In an embodiment, the single chain antibody consists of a heavy chain region having at least 95% sequence identity SEQ ID NO: 4. In another embodiment, the single chain antibody consists of a heavy chain region having SEQ ID NO: 4.

In an embodiment, the isolated antibody or antigen-binding fragment further comprises an Fc region covalently linked, e.g., fused to the heavy chain variable region. The Fc region is preferably not the Fc region associated with the heavy chain variable region in nature, such as a murine Fc sequence.

The isolated antibody or antigen-binding fragment optionally further comprises a light chain. Exemplary light chains include:

```
                                              SEQ ID NO: 5
MYRMQLLSCIALSLALXXNSQSVLTQPPSSSGTPGQ--RVTISCSGSSSNIGSN-TVNWY

QQLPGTAPKLLIYDNSNRPSGVPDRFSGSKSGTSASLAISGLRSEDEADYYCAAWDDSLN

GHWVFGGGTQLTVLSVLGQPKAAPSVILFPPSSEELQANKATLVCLISDFYPGAVIVAWK

ADSSPVKAGVETTTPSKXSNNKYAASXYLSLTPEQXKSHRKLQLPRSRMKGAPWKRQWPP

TECS
```

-continued

```
                                                         SEQ ID NO: 6
MYRMQLLSCIALSLALVTNSQSVLTQPPSASGTPGQ--SVTISCSGSTSTIGSNY-VFWY

RQLPGTAPKLLVYDNTNRPSGVPDRFSGSKSGTSASLAISGLRSEDEADYYCAAWDDSL-

SGRVFGGGTQLTVLSVLGQPKAAPSVTLFPPSSEELQANKATLVCLISDFYPGAVTVAWK

ADSSPVKAGVETTTPSKQSNNKYAASSYLSLTPEQWKSHRSYSCQV-THEGSTVEKTVAP

TECS

SEQ ID NO: 7
MYRMQLLSCIALSLALVTNSQSVLTQPPSVSGAPGQ--RVTISCTGSSSNIGADYDVHWY

QQLPGTAPKLLIYDNTNRPSGVPDRFSGSKSGTSASLAITGLQTEDEADYYCQSYDGSL-

GEGVFGGGTQLTVLSVLGQPKAAPSVILFPPSSEELQANKATLVCLISDFYPGAVIVAWK

ADSSPVKAGVETTTPSKQSNNKYAASSYLSLTPEQWKSHRSYSCQV-THEGSTVEKTVAP

TECS

SEQ ID NO: 8
MYRMQLLSCIALSLALVTNSQSVLTQPPSVSGAPGQ--RVTISCTGSSSNIGAGYDVQWY

QQLPGTAPKLLIYGNSNWPSGVPDRFSGSKSGTSASLAITGLQAEDEAVYHCQTYDSSL-

SGSVFGGGIKLIVLSVLGQPKAAPSVILFPPSSEELQANKATLVCLISDFYPGAVIVAWK

ADSSPVKAGVETTTPSKQSNNKYAASSYLSLTPEQWKSHRSYSCQV-THEGSTVEKTVAP

TECS
```

An antibody or antigen-binding antibody fragment can have a label or detectable moiety attached, e.g., covalently attached, thereto. A "label" or a "detectable moiety" is a composition detectable by spectroscopic, photochemical, biochemical, immunochemical, chemical, or other physical means. Exemplary labels include radioactive label (such as $^{3}H$, $^{14}C$, $^{32}P$, $^{33}P$, $^{35}S$, $^{90}Y$, $^{99}Tc$, $^{111}In$, $^{125}I$, $^{131}I$, $^{177}Lu$, $^{166}Ho$, and $^{153}Sm$), an enzymatic label (such as horseradish peroxidase, alkaline peroxidase, glucose 6-phosphate dehydrogenase, and the like), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like), rhodamine, phycobiliproteins, R-phycoerythrin, quantum dots (e.g., zinc sulfide-capped cadmium selenide), a thermometric label, or an immuno-polymerase chain reaction label.

Alternatively, or in addition, an antibody or antigen-binding antibody fragment can have a therapeutic agent attached, e.g., covalently attached, thereto.

The therapeutic agent can be cytotoxic agent. The cytotoxic agent can be selected from a group consisting of ricin, ricin A-chain, doxorubicin, daunorubicin, taxol, ethiduim bromide, mitomycin, etoposide, tenoposide, vincristine, vinblastine, colchicine, dihydroxy anthracin dione, actinomycin D, diphteria toxin, *Pseudomonas* exotoxin (PE) A, PE40, abrin, arbrin A chain, modeccin A chain, alpha-sarcin, gelonin mitogellin, retstrictocin, phenomycin, enomycin, curicin, crotin, calicheamicin, *Sapaonaria officinalis* inhibitor, maytansinoids, and glucocorticoidricin. The therapeutic agent can be a radioactive isotope such as $^{212}Bi$, $^{131}I$, $^{111}In$, $^{90}Y$ and $^{186}Re$.

The antibodies and antigen-binding fragments described herein can be used to detect and quantitate (e.g., by use of a standard curve) the presence of HSP90.

The antibodies and antigen-binding fragments can be used in conventional immunoassay formats, such as enzymatic immunoassays (EIA), enzyme-linked immunosorbent assays (ELISA), Western blotting, immunohistochemistry (IHC), immunoprecipitation, immunoelectrophoresis, dipstick (antibody, antigen-binding fragment, or immunoconjugate coupled to a solid support), an assay strip, radioimmunometric assays (RIA), immunoturbidimetric assays, and others known in the prior art. Immunofluorescence assays using an antibody or antibody fragment that specifically binds HSP90 may also be employed. Such assays include confocal microscopy using a fluorescently labeled primary or secondary antibody.

In any of the illustrative assays, the biological sample can be provided as a known or unknown quantity of urine, semen, seminal fluid, synovial fluid, saliva, exhaled breath condensate, tissue, blood, or a blood derived product such as serum or plasma.

Biological samples useful in a disclosed method can be isolated, analyzed in vitro and include any cell preparation or tissue preparation that can be fixed and mounted on a solid surface. Exemplary samples include, without limitation, blood smears, cytocentrifuge preparations, cytology smears, core biopsies, fine-needle aspirates, or tissue sections (e.g., cryostat tissue sections or paraffin-embedded tissue sections). Exemplary biological samples may be isolated from normal cells or tissues, or from neoplastic cells or tissues. Neoplasia is a biological condition in which one or more cells have undergone characteristic anaplasia with loss of differentiation, increased rate of growth, invasion of surrounding tissue, and which cells may be capable of metastasis.

Exemplary neoplastic cells or tissues may be isolated from solid tumors, including breast carcinomas (e.g., lobular and duct carcinomas), sarcomas, carcinomas of the lung (e.g., non-small cell carcinoma, large cell carcinoma, squamous carcinoma, and adenocarcinoma), mesothelioma of the lung, colorectal adenocarcinoma, stomach carcinoma, prostatic adenocarcinoma, ovarian carcinoma (such as serous cystadenocarcinoma and mucinous cystadenocarcinoma), ovarian germ cell tumors, testicular carcinomas and germ cell tumors, pancreatic adenocarcinoma, biliary adenocarcinoma, hepatocellular carcinoma, bladder carcinoma (including, for instance, transitional cell carcinoma, adenocarcinoma, and squamous carcinoma), renal cell adenocarcinoma, endometrial carcinomas (including, e.g., adenocarcinomas and mixed Mullerian tumors (carcinosarcomas)), carcinomas of the endocervix, ectocervix, and vagina (such as adenocarcinoma and squamous carcinoma of each of same), tumors of the skin (e.g., squamous cell carcinoma, basal cell carcinoma, melanoma, and skin appendage tumors), esophageal carcinoma, carcinomas of the nasopharynx and oropharynx (including squamous carcinoma and adenocarcinomas of same), salivary gland carcinomas, brain and central nervous system tumors (including, for example, tumors of glial, neuronal, and meningeal origin), tumors of peripheral nerve, soft tissue sarcomas and sarcomas of bone and cartilage.

Further included is a method for the treatment of a patient in need of therapy, characterized by administering to the patient a therapeutically effective amount of an antibody that binds HSP90 as described herein. The antibodies are useful in methods of treating diseases responsive to anti-HSP90 therapy, including cancers, specifically late stage disseminating cancers.

The antibodies may be used in the treatment of cancer. The term "cancer" as used herein may be, for example, lung cancer, non-small cell lung (NSCL) cancer, bronchioloalveolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma, lymphoma, lymphocytic leukemia, including refractory versions of any of the above cancers, or a combination of one or more of the above cancers. Specific cancers include aggressive melanoma, bladder and ovarian cancers.

To express the antibodies, or antibody fragments thereof, DNAs encoding partial or full-length light and heavy chains obtained by standard molecular biology techniques are inserted into expression vectors such that the genes are operatively linked to transcriptional and translational control sequences. In this context, the term "operatively linked" means that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain encoding genes, the recombinant expression vectors carry regulatory sequences that control the expression of the antibody chain genes in a host cell. The term "regulatory sequence" includes promoters, enhancers and other expression control elements (e.g., polyadenylation signals) that control the transcription or translation of the antibody chain genes. The selection of regulatory sequences may depend on such factors as the choice of the host cell to be transformed, the level of expression of protein desired, and the like. Examples of regulatory sequences for mammalian host cell expression include viral elements that direct high levels of protein expression in mammalian cells, such as promoters or enhancers derived from cytomegalovirus (CMV), Simian Virus 40 (SV40), adenovirus, (e.g., the adenovirus major late promoter (AdMLP)) and polyoma. Alternatively, nonviral regulatory sequences may be used, such as the ubiquitin promoter or β-globin promoter.

In addition to the antibody chain genes and regulatory sequences, the recombinant expression vectors may carry additional sequences, such as sequences that regulate replication of the vector in host cells (e.g., origins of replication) and selectable marker genes.

For expression of the light and heavy chains, the expression vector(s) encoding the heavy and light chains is transfected into a host cell by standard techniques. The term "transfection" encompasses a wide variety of techniques commonly used for the introduction of exogenous DNA into a prokaryotic or eukaryotic host cell, e.g., electroporation, calcium-phosphate precipitation, DEAE-dextran transfection, and the like. Although it is theoretically possible to express the antibodies in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Examples of mammalian host cells for expressing the recombinant antibodies include Chinese Hamster Ovary (CHO cells), NSO myeloma cells, COS cells, HKB11 cells and SP2 cells.

Also provided are pharmaceutical compositions comprising therapeutically effective amounts of antibody and a pharmaceutically acceptable carrier. "Pharmaceutically acceptable carrier" is a substance that may be added to the active ingredient to help formulate or stabilize the preparation and causes no significant adverse toxicological effects to the patient. Examples of such carriers are well known to those skilled in the art and include water, sugars such as maltose or sucrose, albumin, salts such as sodium chloride, etc.

Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. The composition may be formulated for parenteral injection. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. In some cases, it will include isotonic agents, for example, sugars, polyalcohols such as mannitol, sorbitol, or sodium chloride in the composition.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, some methods of preparation are vacuum drying and freeze-drying (lyophilization) that yield a powder of the active ingredient plus any additional desired ingredient from a previously sterile-filtered solution thereof.

The invention is further illustrated by the following non-limiting examples.

EXAMPLES

Methods

Cloning, synthesis and purification of heavy chain antibodies: Forty six different variable heavy chain clones were selected from previously established cDNA libraries. Variable heavy chain clones were sequenced and analyzed using IMGT/V-QUEST to determine the V, D and J gene segment usage. Mutations within the complementarity determining regions (CDRs 1, 2 and 3) as well as the framework regions (FRs 1, 2, 3 and 4) were determined for each of the sequences in comparison to their respective germline sequences. The variable heavy chain sequences were subcloned from the pCR®T7/CT-TOPO® (Life Technologies, NY, USA) plasmid into the mammalian expression vector pCMV6-AC-FC-S (OriGene technologies, MD, USA) using the following strategy. The variable heavy chain sequences were amplified by two rounds of PCR. The first round of PCR was performed using forward primer 5'-TTCGGCGATCGCCATGCAGGTGCAGCTGGTGSAGTCTGG-3' (SEQ ID NO: 9) and reverse primer 5'-GCCTTGGAAG-TACAGGTTCTCACCGGTACGCGTAGAATCGAGAC-CGAG-3' (SEQ ID NO: 10), while the second round was performed using the same forward primer and reverse primer 5'-TGGGCTCGAGGCCTTGGAAGTACAGGT-TCTCACCGGTACGCG-3' (SEQ ID NO: 11).

PCR products were purified using QIAquick® PCR purification kit (QIAGEN, CA, USA) as per the manufacturer's instructions. Purified PCR products and the pCMV6-AC-FC-S plasmid were digested with AsiSI and XhoI (New England Biolabs, MA, USA) restriction enzymes for 1 h at 37° C. PCR products were ligated into the pCMV6-AC-FC-S plasmid and the resultant transformants were screened by restriction digestion analysis. For this study, 8 variable heavy chain domain clones derived from four breast cancer patients were selected.

Purified plasmid DNA containing the variable heavy chain sequences were transfected into HEK293T cells. After 12-16 h, cells were washed with PBS and refed with serum free media. 48 h after refeeding, conditioned media was collected and centrifuged at 300 g to pellet dead cells. The supernatant was filtered through 0.22 µm filter (polyethersulfone membrane, Millipore, MA, USA) and mixed with equal volume of PBS. Heavy chain antibodies were purified by protein A affinity chromatography using a 1 mL cartridge connected to an AKTA Purifier 10 system. The purified heavy chain antibodies were then concentrated and buffer exchanged using centrifugal concentrators (Microcon YM-30, Millipore). Total protein content was determined by reading absorbance at 280 nm and using the calculated extinction coefficients for each of the individual HCAbs.

Cells and cell culture: All the different cells used in this study were obtained from American Type Culture Collection (ATCC, VA, USA). HMEC and MCF10A cells were cultured in mammary epithelial cell growth medium (MEGM-Lonza) supplemented with 50 units/mL of penicillin and 50 µg/mL of streptomycin, while HEK293T, MCF7 and MDA-MB-231 cells were cultured in Dulbecco's modified Eagle's medium (DMEM—Invitrogen) supplemented with 10% fetal bovine serum, 50 units/mL of penicillin and 50 ng/mL of streptomycin Antibodies: Antibodies against HSP90 (4877), clathrin heavy chain (4796), calnexin (2679) and cleaved caspase-3 (9661) were purchased from Cell Signaling Technology, MA, USA. E-cadherin antibody (sc-7870) was purchased from Santa Cruz Biotechnology, TX, USA. Antibodies against CD31 (553370) and CD44-FITC (555478) were purchased from BD Biosciences, CA, USA. Alexa Fluor® 488 anti-mouse (A11001), Alexa Fluor® 594 anti-mouse (A11005), Alexa Fluor® 594 anti-rabbit (A11012) and Alexa Fluor® 594 anti-rat (A21209) antibodies were purchased from Life technologies, NY, USA. Biotinylated anti-mouse antibody was purchased from Vector laboratories, CA, USA.

Flow cytometry: Cells were trypsinized with 0.05 trypsin-EDTA (Life Technologies) and $0.5*10^6$ cells for each cell type were used for the analysis. Cells were washed thrice with Hank's balanced salt solution containing 3% fetal bovine serum and 1 mM EDTA (FACS buffer) and incubated on ice with 10 µg of respective HCAbs for 30 min. Bound HCAbs were detected using Alexa Fluor® 488 anti-mouse IgG antibody. Propidium iodide was used to detect the population of dead cells. Samples were analyzed using a BD LSR II flow cytometer and histograms were prepared using FlowJo® software.

Immunofluorescence (IF) analysis: Cells were grown in 4-well or 8-well chamber slides (Millipore) in respective media. Cells were washed with PBS and fixed with 4% paraformaldehyde (Electron Microscopy Sciences, PA, USA). Permeabilization was performed by incubating cells with 0.1% Triton X-100 for 15 min. 5 µg of HCAbs were used to stain each cell line and bound HCAbs were detected using Alexa Fluor® 488 anti-mouse IgG antibody.

Methanol/acetone fixed normal (n=11) and tumor breast tissues (n=14) were used, which included 6 patient matched normal and tumor tissues. The tissues were blocked with 3% bovine serum albumin and incubated with 5 µg of HCAb2 per section. Bound HCAb2 was detected using Alexa Fluor® 488 anti-mouse IgG antibody.

MDA-MB-231 xenograft tumor sections and normal mouse tissue sections were fixed with ice cold acetone for 20 min at −20° C. HCAb2 localization was detected using Alexa Fluor® 488 anti-mouse IgG antibody. Anti-CD44 (1:100), anti-CD31 (1:100) and anti-calnexin (1:50) were used in the respective experiments.

In all the experiments, nuclei were stained with 4',6-Diamidino-2-Phenylindole, Dihydrochloride (DAPI) and the images were taken using Zeiss LSM 780 confocal microscope. Images were edited using ZEN 2012 (black edition) as well as Adobe Photoshop CS4.

Immunohistochemistry (IHC) and Histoscoring: BR1009 breast tissue microarrays were purchased from US Biomax, Inc., MD, USA. Each slide contained cores from 35 invasive ductal carcinoma tissues as well as 4 normal adjacent/normal tissues. Slides were deparaffinized, rehydrated and subjected to heat-induced antigen retrieval process by heating the slides to 95° C. in citrate buffer, pH 6.0 (Thermo Scientific, MA, USA). Endogenous peroxidase activity was blocked with 3% hydrogen peroxide. Slides were incubated overnight at 4° C. with 12 µg of the HCAbs followed by biotinylated anti-mouse antibody. Slides were developed using DAB (Thermo Scientific) chromogen and the nuclei were counter stained with methyl green (Vector laboratories).

Histoscoring was used to quantify the immunohistochemical staining as described previously. Staining was visually evaluated and intensity scores ranging from 0-3 (3 being strongest staining) were given. The percentage of cells positive for each intensity score was also noted. To obtain the histoscores, intensity scores were multiplied by the respective percent of cells. The resulting values for all intensity scores were added to give the final histoscores for that tissue. Histoscoring was performed by three independent scorers and the scores were averaged.

Cell lysates and cell fractionation: Cells were scraped in 1% Triton™ X-100/PBS or 1% Triton™ X-100+0.1% SDS/PBS lysis buffers supplemented with 1 mM EDTA, 0.2 mM sodium orthovanadate and fresh protease inhibitor cocktail. Nuclei were spun out and the supernatants were used for immunoprecipitation assays.

Plasma membrane protein isolation kit (SM-005, Invent Biotechnologies Inc., MN, USA) was used to fractionate cells to obtain nuclei, cytosol, organelles and plasma membrane fractions. Three P150 mm dishes with 90% confluent cells were used to obtain cytosolic and plasma membrane fractions as per the manufacturer's instructions. The plasma membrane protein pellet was resuspended in 1% Triton™ X-100+0.1% SDS/PBS buffer while the cytosol was brought to a final concentration of 1% Triton™ X-100 and 0.1% SDS.

Xenograft tumor pieces were placed in 500 µL of 1% Triton™ X-100+0.1% SDS/PBS lysis buffer supplemented with 0.2 mM sodium orthovanadate and fresh protease inhibitor cocktail (1:100) and homogenized using polytron homogenizer for 30 sec −1 min on ice. Homogenates were spun at 14,000 rpm for 20 min at 4° C. and supernatants were used for immunoprecipitation.

Immunoprecipitation (IP): Cell lysates or tumor lysates were pre-cleared with protein A beads and incubated overnight with 20 µg of HCAbs at 4° C. Protein A beads were used to pull down HCAb-antigen complexes. Beads were boiled in sample loading buffer and the proteins were resolved on a reducing SDS-PAGE gel. Proteins in the gel were stained with SYPRO® Ruby stain (Life Technologies) as per the manufacturer's instructions.

Recombinant human HSP90β (ALX-201-147-025) was purchased from Enzo life sciences, NY, USA and resuspended in PBS. 1 µg of HSP90β in PBS along with bovine serum albumin was mixed with either 1% Triton™ X-100+ 0.1% SDS or 1% Triton™ X-100+1 SDS buffers and incubated overnight with 10 µg of HCAb1 and HCAb2. Immunoprecipitation was performed as explained above.

Mass spectrometry: All the analyses were performed at Keck MS and proteomics resource facility (Yale School of Medicine). In-gel trypsin digestion of proteins was performed and the peptides were analyzed using LC-MS/MS on a Thermo Scientific LTQ-Orbitrap XL mass spectrometer. Mascot search algorithm was used to identify the proteins from SwissProt database.

In vitro scratch assay: MDA-MB-231 cells were grown to 90% confluency in 6-well plates and serum starved for 2 h following which scratches were made using 200 µl pipet tips. Wells were washed with PBS to get rid of floating cells and incubated with 1% fetal bovine serum containing media. Cells were imaged and were termed as T=0 h images. 5 µg of HCAb1 and HCAb2 were added to the respective wells and cells were imaged after 19 h (T=19h images).

Acellular areas at T=0 h and T=19 h were determined for each well using Image-Pro® Plus 5.1 software. The experiment was performed in four independent wells for each treatment and the area values were averaged for the 4 wells. Average acellular area at T=0 h for each treatment was set to be 100% and the areas at T=19 h were normalized to the corresponding average acellular area at T=0 h. Percent acellular area remaining at T=19 h was calculated accordingly.

MDA-MB-231 xenograft tumor model: MDA-MB-231 cells were trypsinized and a suspension of $1*10^7$ cells/mL in DMEM was prepared. Cells were centrifuged and resuspended in 70% matrigel (BD biosciences)+30% DMEM. $1*10^6$ cells were injected subcutaneously into the mammary fat pad of 5 female NOD scid gamma (NSG) mice. After 24 days xenograft tumors ranged from 300-500 mm$^3$ and mice were retro-orbitally injected with 12 µg of purified and sterile filtered HCAb1 (n=2) and HCAb2 (n=3). After 2 h, 6 h and 24 h, mice were euthanized and tumors along with various normal tissues were harvested. All animal experiments were approved by the University of Connecticut Health Center's Institutional Animal Care and Use Committee.

Statistical analysis: Data from individual experiments was represented as mean±standard deviation. Statistical analyses were performed using GraphPad Prism 5.01 and significance was determined by one-way ANOVA analysis and/or 2-tailed Student's t test (*=p≤0.05).

Example 1: HCAb2 Preferentially Bound to the Surface of MDA-MB-231 Cells

Previously we had generated antigen-driven variable heavy chain cDNA libraries from sentinel lymph nodes of breast cancer patients. The cDNA libraries consisted of over 1100 individual variable heavy chain sequences. Using the previously mentioned selection criteria, we were able to determine the variable heavy chain sequences that were generated in response to antigens. The selection strategy included identifying variable heavy chain sequences that were part of clonal groups as well as containing replacement mutations within the complementarity determining regions. Both these attributes are hallmarks of B-cells that have been activated in response to antigens. Using this selection strategy, we were able to identify 46 different variable heavy chain sequences for further analysis and subcloned them into a mammalian expression vector. In this study, we selected 8 (out of 46) variable heavy chain sequences (HCAb1-8) derived from 4 breast cancer patients. Variable heavy chain sequences were analyzed using IMGT/V-QUEST to determine the V, D and J gene segment usage. Based on the highest matching score, HCAb1 is made up of V3-23, D6-19 and J4 and HCAb2 is made up of V1-18, D5-18 and J4 gene segments. Replacement mutations in comparison to the respective germline VDJ segments were determined within the CDRs (1, 2 and 3) and FRs (1, 2, 3 and 4). As depicted in FIG. 1A, both HCAb1 (SEQ ID NO: 12) and HCAb2 (SEQ ID NO: 4) contain replacement mutations (asterisks) with HCAb2 containing a larger number of mutations. We synthesized and purified the bivalent HCAbs and observed that the monomeric molecular weights of the HCAbs on a reducing gel were closer to 50 kDa (FIG. 1B).

```
                                              (SEQ ID NO: 12)
QVQLVQSGGGLVQPGGSLRLSCAASGFTFSSYAMSWVRQAPGKGLEWVSA
ISGSGGSTYYADSVKGRFTISRDNSKNTLYLQMNSLRAEDTAVYYCARQE
GQWLVQIDYWGQGTLVTVSS
```

We screened the HCAbs against MCF10A (non-tumorigenic cells), MCF7 (estrogen receptor positive cancer cells) and MDA-MB-231 (triple negative breast cancer cells) by flow cytometry to ensure stringent identification of cell surface targeting HCAbs. Moreover, flow cytometry allowed us to quantitatively determine the size of the cell population targeted by the HCAbs. As seen in FIG. 1C, HCAb2 (orange peak) bound strongly to MDA-MB-231 cells (51.1% positively stained cells) and showed weak binding to MCF10A (4.37%) and MCF7 (0.94%) cells (FIG. 1C). HCAb1 and HCAb8 did not bind to the surface of any of the 3 cell lines and were used as controls for future experiments.

To visualize the staining pattern, we performed immunofluorescence analysis on primary normal human mammary epithelial cells (HMEC), MCF7 and MDA-MB-231 cells. HCAb1 showed no staining on the surface of HMEC (FIG. 1D), MCF7 (FIG. 1E) and MDA-MB-231 cells (FIG. 1F), while HCAb2 showed no staining on HMECs (FIG. 1G) and weak staining on MCF7 cells (FIG. 1H); we observed definitive punctate staining on the surface of MDA-MB-231 cells (FIG. 1I). In order to determine if the antigen for HCAb2 was also present within the cells, HCAb2 was incubated with permeabilized cells. We observed that HCAb2 showed reduced cytoplasmic staining with HMEC (FIG. 1M), while strong cytoplasmic staining with MCF7 (FIG. 1N) and MDA-MB-231 cells was observed (FIG. 1O). It appeared that the antigen for HCAb2 is present in the cytoplasm of all 3 cell lines; however significant amount was present on the cell surface of MDA-MB-231 cells. HCAb1 did not show cell surface staining but showed strong perinuclear staining with HMECs (FIG. 1J), MCF7 (FIG. 1K) and MDA-MB-231 cells (FIG. 1L). Both the screening methods revealed that HCAb2 preferentially bound to the surface of MDA-MB-231 cells (FIGS. 1C and 1I) and not to normal or MCF7 cells (FIGS. 1C and 1G).

Example 2: HCAb2 Bound Strongly to Primary Breast Tumor Tissues in Comparison to Normal Tissues We then wanted to validate our results from cell line analysis by screening HCAb2 on primary human breast normal and tumor tissues. We screened HCAb2 along with HCAb1 and HCAb8 as controls on a breast tissue microarray containing invasive ductal carcinoma tumor (n=35) and normal tissues (n=4). We observed that HCAb8 did not bind to any of the tissues (FIG. 8A-8C), while HCAb1 bound to the normal tissues (representative image, FIG. 8D) as well as the tumor tissues (FIG. 8E-8F) equally. HCAb2 bound weakly to normal tissues (representative image, (FIG. 8G) while strongly to tumor tissues (FIG. 8H-8I). Interestingly, the tumor staining patterns with HCAb2 varied from isolated cells (FIG. 8H) to homogenous staining (FIG. 8I) and was independent of TNM stage of the tumor cases. Histoscoring was used to quantify the potential differences in the staining intensities between normal and tumor tissues. As depicted in FIG. 8J, HCAb1 bound to the normal and tumor tissues equally, while HCAb2 bound to the tumor tissues strongly in comparison to normal tissues (p=0.0134).

To further determine the specificity of HCAb2, we screened our in-house cohort of fresh frozen human breast tissue samples. Our cohort consisted of 31 ER+breast tumor cases with 12 matched normal samples, 5 triple negative tumor cases with 4 matched normal samples and 4 HER2 overexpressing tumor cases with 3 matched normal samples. Immunofluorescence analysis revealed that HCAb2 showed no staining or weak staining on all of the 26 normal breast tissues (FIG. 2A-2D, 2M-2O and FIG. 8K-8M). But the tumor samples revealed heterogenous staining patterns ranging from few positively stained cells to big clusters of positively stained cells. 12 out of the 31 ER+tumor samples, 3 out of the 5 triple negative tumor samples and 1 out of the 4 HER2 overexpressing tumor samples showed positive staining with HCAb2. For the 3 tumor types, around 5-10% of the tumor epithelial cell populations were found to be positively stained by HCAb2. This would indicate that HCAb2 bound specifically to a subset of tumor cells. Also in a majority of the tumor samples, HCAb2 staining was observed to be punctate in nature (FIG. 2E, 2G-2H, 2K-2L and FIG. 8N-8P), similar to the pattern observed with MDA-MB-231 cells (FIG. 1I). As shown in FIG. 2E, 2G-2H and FIG. 8N-8O, HCAb2 staining on the ER+tumor samples was found to be selective to the epithelial cells as evidenced by positive E-cadherin staining. HCAb2 also preferentially bound to the tumors (FIG. 2E-2F and FIG. 8N) in comparison to the respective patient-matched normal tissues (FIG. 2A-2B and FIG. 8K). In addition, we observed that HCAb2 showed cell surface staining on the tumor tissues (FIG. 2E, 2G, 2H and FIG. 8N-8O). Interestingly for some of the ER+tumor samples, HCAb2 showed strong staining on E-cadherin negative epithelial cells (FIG. 2I-2L). This can be clearly observed in FIG. 2I as well as FIG. 2J (magnified view), wherein HCAb2 strongly stained the E-cadherin negative cells while weakly stained the E-cadherin positive cells within the same cluster.

HER2 overexpressing tumor samples did not show strong staining with HCAb2 and only one of the 4 samples revealed moderate staining (FIG. 8P) with HCAb2. With respect to the triple negative tumor samples, HCAb2 showed moderate staining (FIG. 2P) to strong staining (FIG. 2Q-2R) on N-cadherin positive cells. Similar to ER+tumor samples, HCAb2 showed preferentially staining on triple negative tumor tissues (FIG. 2P-2R) in comparison to the respective patient matched normal tissues (FIG. 2M-2O). From the immunohistochemical and immunofluorescence analyses on primary breast tissues, it was evident that HCAb2 preferentially bound to tumor tissues in comparison to normal tissues and thereby enabled HCAb2 to be an ideal candidate for further characterization.

Example 3: Identification of the Target Antigens for HCAb1 and HCAb2

In order to determine the antigens recognized by the HCAbs, we performed immunoprecipitation of the antigens followed by protein identification using mass spectrometry. We chose MDA-MB-231 cell lysates since the respective target antigens for both HCAb1 (FIG. 1L) and HCAb2 (FIGS. 1C, 1I and 1O) were abundant in MDA-MB-231 cells. The immunoprecipitated proteins were run on a reducing SDS-PAGE gel and visualized using SYPRO® Ruby stain. We observed that the immunoprecipitation with HCAb1 showed a specific band (~MW 200 kDa) from 1% Triton™ X-100 lysates, while immunoprecipitation with HCAb2 did not show any specific band under these conditions (FIG. 3A). On the other hand, immunoprecipitation with HCAb2 showed a specific band (~MW 90 kDa) from 1% Triton™ X-100 lysates supplemented with 0.1% SDS (FIG. 3B). Furthermore, these buffer conditions were unfavorable for HCAb1 to immunoprecipitate the band seen previously (FIG. 3A) in the buffer lacking SDS. Multiple repeats revealed the same results and led us to conclude that the interaction between HCAb1 and its antigen is abolished in the presence of 0.1% SDS, while the interaction between HCAb2 and its antigen requires the presence of 0.1% SDS. This would suggest that the antigen for HCAb2 could either be Triton™ X-100 insoluble and requires SDS to solubilize or that the epitope on the target antigen is made accessible only in the presence of SDS.

The specific gel bands (*) observed in FIGS. 3A and 3B were excised and the tryptic peptides were analyzed by mass spectrometry. Peptides identified from the analysis were used to search the SwissProt database to obtain the list of target proteins. Tables 1 and 2 list the top five proteins identified from the HCAb1 and HCAb2 immunoprecipitated bands, respectively. Keratin proteins seen in the results are typical contaminants introduced during the handling of the gel bands. The top hit for HCAb1 was clathrin heavy chain 1 (CLTC) protein with 40.7 percent coverage of the protein from the identified peptides (Table 1). The molecular weight of the CLTC protein is 191.493 kDa, which is similar to the molecular weight of the excised gel band (FIG. 3A), suggesting that the target antigen for HCAb1 could be CLTC protein. Similarly, the top hits for HCAb2 were heat shock protein HSP90-beta and heat shock protein HSP90-alpha with percent peptide coverages of 51.7 and 40.6, respectively (Table 2). The molecular weight of the excised band (~90 kDa) (FIG. 3B) overlaps with the molecular weights of both the HSP90 isoforms (Table 2), suggesting that the target antigen for HCAb2 could be HSP90.

TABLE 1

List of the top five proteins identified from the HCAb1 specific gel band

| Score | Gene name | Swiss-prot accession no. | Protein Name | MW (Da) | % Coverage |
|---|---|---|---|---|---|
| 2366 | CLTC | Q00610 | Clathrin heavy chain 1 | 191493 | 40.7 |
| 776 | KRT1 | P04264 | Keratin 1 | 66027 | 24.4 |
| 720 | — | — | Unnamed protein product | 59492 | 27.3 |
| 682 | KRT1 | P04264 | Keratin 1 | 66026 | 24.4 |
| 463 | KRT2 | P35908 | Epidermal cytokeratin 2 | 65825 | 27.8 |

TABLE 2

List of the top five proteins identified from the HCAb2 specific gel band

| Score | Gene name | Swiss-prot accession no. | Protein Name | MW (Da) | % Coverage |
|---|---|---|---|---|---|
| 1812 | HSP90AB1 | P08238 | Heat shock protein HSP 90-beta | 83212 | 51.7 |
| 1007 | KRT16 | P08779 | Keratin, type I cytoskeletal 16 | 51236 | 45 |
| 1004 | HSP90AA1 | P07900 | Heat shock protein HSP 90-alpha | 84607 | 40.6 |
| 980 | KRT6C | P48668 | Keratin, type II cytoskeletal 6C | 59988 | 30.7 |
| 970 | KRT6A | P02538 | Keratin, type II cytoskeletal 6A | 60008 | 30.7 |

Example 4: Validation of the Target Antigens for HCAb1 and HCAb2

Clathrin heavy chain was found to be the putative target antigen for HCAb1 (Table 1). For validation of the antigen, we performed co-localization immunofluorescence analysis on MCF7 cells using HCAb1 and a commercial anti-CLTC antibody. As seen in FIG. 9A-9D, HCAb1 and the commercial antibody co-localized to the pen-nuclear region, suggesting that HCAb1 binds to clathrin heavy chain.

HSP90 was found to be the antigen for HCAb2 from the mass spectrometric analysis (Table 2). HSP90 is an intracellular molecular chaperone that aids in the appropriate folding of a wide variety of proteins. There are four different isoforms of HSP90 which include HSP90α, HSP90β (cytosolic isoforms), Grp94 (endoplasmic reticulum isoform) and TRAP1 (mitochondrial isoform). In addition to its cytosolic localization, HSP90 has been shown to be present on the plasma membrane as well as outside of the cells. Indeed HSP90 has previously been observed on the surface of MDA-MB-231 cells. In order to validate HSP90 to be the target antigen for HCAb2, we fractionated MDA-MB-231 cells to obtain plasma membrane and cytosolic fractions that were subsequently used for immunoprecipitation with HCAb2. Immunoprecipitated proteins were run on a reducing SDS-PAGE gel and immunoblot analysis was performed using a commercial HSP90 antibody. The commercial HSP90 antibody used for the immunoblot analysis detected the levels of total HSP90 and does not discriminate between the alpha or beta isoforms. As seen in FIG. 4A, HCAb2 pulled down HSP90 from both the fractions with higher amounts being pulled down from the cytosolic fraction. This difference in the amount of HSP90 being pulled down could be attributed to the abundance of HSP90 in the cytosol in comparison to the plasma membrane. Equal amounts of HCAb2 were pulled down in both immunoprecipitations as detected with anti-mouse antibody (FIG. 4A) to control for antibody amounts.

The list of proteins identified for HCAb2 contained both HSP90α and HSP90β isoforms with HSP90β being the highest scoring protein (Table 2). This could suggest that HCAb2 binds to both the isoforms or that the list of peptides identified from the mass spectrometric analysis were common to both the isoforms. Indeed analyzing the mass spectrometric results revealed a total of 45 peptides that matched to the HSP90 protein. Of the 45 peptides, 3 peptides were unique to HSP90α, while 15 peptides were unique to HSP90β and the remaining 27 peptides were common to both the isoforms. This suggests that the antigen for HCAb2 could be HSP90β owing to the identification of a higher percentage of unique peptides. To test this, we used recombinant human HSP90β (highest scoring protein from Table 2) to determine the specificity of HCAb2. HCAb1 and HCAb2 were examined for their ability to immunoprecipitate HSP90β and the presence of HSP90β detected using the commercial HSP90 antibody. As seen in FIG. 4B, HCAb2 pulled down HSP90β strongly in the presence of 1% Triton™ X-100 and 0.1% SDS. This interaction was abolished when the SDS concentration was elevated from 0.1% to 1%. A faint diffuse band was seen from the immunoprecipitation with HCAb1 (1% Tx100+0.1% SDS) as well as for both HCAb1 and HCAb2 (1% Tx100+1 SDS), which could be due to a non-specific interaction. Taken together these results validate that the target antigen for HCAb2 is HSP90 and that HCAb2 is capable of recognizing both the cytosolic and plasma membrane associated HSP90 protein.

Example 5: HCAb2 Reduced Migration of MDA-MB-231 Cells in a Scratch Assay

Cell surface and extracellular localized HSP90 has been implicated in increased invasiveness of tumors. Levels of secreted HSP90α have been shown to be positively correlated with the malignancy of different tumors. Cell impermeable anti-HSP90 antibody and a cell impermeable small molecule inhibitor of HSP90 have both been shown to reduce tumor cell motility and invasion. Since HCAb2 binds to cell surface HSP90, we aimed to determine if HCAb2 could reduce the migration of MDA-MB-231 cells. An in vitro scratch assay was performed with MDA-MB-231 cells in the presence of HCAb1 and HCAb2 and compared to untreated controls. Representative images were taken at T=0 h and T=19 h to determine the differences in the migration between the different treatments. All the wells had similar scratch area at T=0 h (FIG. 5A-5C) while at T=19 h, HCAb2 treated wells (FIG. 5F) showed reduced migration of cells into the acellular area in comparison to untreated (FIG. 5D) or HCAb1 (FIG. 5E) treated wells. In order to quantify the differences in the migration, we determined the acellular area at 0 h as well as at 19 h. Percent acellular area remaining after 19 h was determined and values from 4 different wells were averaged. As seen in FIG. 5G, the percent acellular area remaining after 19 h was highest in the HCAb2 treated cells (68.46%) and lowest in the untreated cells (48.29%), while HCAb1 treated cells had 60.3% of the acellular area still remaining. This reduction could be due to internalization of HCAb1 leading to an indirect effect on migration. The percent acellular area remaining at 19 h between untreated and HCAb1 treated cells was not significantly different (p=0.1336) nor was the difference between HCAb1 and HCAb2 treated cells (p=0.1124). Percent acellular area remaining between untreated and HCAb2 treated cells was significantly different (p=0.0173), suggesting that HCAb2 was able to reduce the migration of MDA-MB-231 cells. Therefore, binding of HCAb2 to HSP90 could inhibit the invasiveness of MDA-MB-231 cells at a moderate yet significant level.

Example 6: HCAb2 Preferentially Localized to MDA-MB-231 Xenograft Tumors

All the experiments thus far have shown that HCAb2 is a tumor specific antibody (FIG. 1, 2 and FIG. 8) that can bind to cell surface HSP90 (FIG. 4A) and inhibit the invasiveness of tumor cells in vitro (FIG. 5). Next we wanted to determine if HCAb2 can target tumors in an in vivo tumor model. To examine this, we generated MDA-MB-231 xenograft tumors in female NSG mice and let the tumors reach 300-500 mm$^3$. Following which, we retro-orbitally injected 12 μg of HCAb1 and HCAb2 into the circulation of tumor-bearing animals. After 2 h, 6 h and 24 h post-injection of the HCAbs, we harvested the xenograft tumors and normal tissues. We then stained the different tissues to determine the localization of HCAb1 and HCAb2. As expected, HCAb1 did not localize to the xenograft tumors at either of the time points (2 h and 6 h) (FIG. 6A-6B), while HCAb2 was found in the tumors at 2 h (FIG. 6C), 6 h (FIG. 6D) and 24 h (FIG. 6E) time points. We observed that a small population of cells within the tumors stained positively for HCAb2 while a vast majority of the tumors were negative for HCAb2 localization.

We then wanted to examine the bio-distribution of HCAb2 in the other non-tumor mouse tissues. We examined brain, heart, lung, liver and kidney tissues at the 24 h time point to determine the localization of HCAb2. As seen in FIGS. 6F and 6H, there was no detection of HCAb2 in the brain or lung tissues, respectively. Heart (FIG. 6G), liver (FIG. 6I) and kidney tissues (FIG. 6J) revealed weak staining for HCAb2. Staining in the kidney for HCAb2 could be due to renal clearing of the injected HCAb2. These results indicate that HCAb2 preferentially localized to the xenograft tumors in comparison to the normal tissues.

Next we wanted to confirm that HCAb2 was bound to the MDA-MB-231 cells within the xenograft tumors and not to the mouse cells. For this analysis, we stained a 24 h time point tumor section with CD44-FITC as well as Alexa Fluor® 594 anti-mouse IgG antibody to determine the localization of HCAb2 (note: there is little serum mouse IgG in these NSG mice). MDA-MB-231 cells are CD44+ and we observed that the majority of the cells within the xenograft tumors were CD44+ MDA-MB-231 cells (FIG. 6L) with very few mouse cells. We observed that the cells positively stained for HCAb2 were also positive for CD44 staining (FIG. 6L-6N), suggesting that HCAb2 specifically localized to the MDA-MB-231 cells. We also noticed that HCAb2 was present in the cytosol of the targeted cells (FIG. 6N), suggesting that the bound HCAb2 was internalized by the target cells.

We then wanted to determine if the internalization of HCAb2 could lead to apoptosis of the tumor cells at 24 h time point. To this end, we stained the 24 h tumor section with anti-cleaved caspase-3 antibody to identify apoptotic cells. We observed that the cells that showed HCAb2 localization were not apoptotic as evidenced by negative cleaved caspase-3 staining (FIG. 10).

We also wanted to determine if HCAb2 can bind to HSP90 from the xenograft tumor lysates. Xenograft tumor pieces were homogenized and incubated with exogenous HCAb1 and HCAb2. Immunoprecipitated proteins were detected using the commercial HSP90 antibody. From FIG. 11, it was noticed that HCAb2 pulled down HSP90 from all the tumor lysates, while HCAb1 did not pull down HSP90. In summary, we observed that HCAb2 bound preferentially to a small population of MDA-MB-231 xenograft tumor cells in comparison to the normal mouse tissues and also pulled down HSP90 from xenograft tumor lysates.

Example 7: HCAb2 Localized to a Subset of MDA-MB-231 Xenograft Tumor Cells

As seen from FIGS. 6C-6E and 6N, HCAb2 was localized to a small population of MDA-MB-231 cells within the tumors. To determine if the vascularization of the tumor could be responsible for the unique localization of HCAb2, we performed CD31 and HCAb2 staining on a 24 h tumor section (FIG. 7A-7H). We observed that HCAb2 localized (FIG. 7B) to the cells that were in close proximity to the blood vessels (FIGS. 7C and 7D) suggesting that these cells were accessible to HCAb2. But even within this section, we observed cells that were in close proximity to the blood vessels but were not positive for HCAb2 localization. This effect was seen more prominently in other fields of the same tumor (FIG. 7E-7H) wherein the vascularized regions of the tumor (FIGS. 7G and 7H) did not show any HCAb2 localization (FIG. 7F). This result eliminates the possibility that the unique localization of HCAb2 was solely due to reduced accessibility to the tumor cells in specific areas.

We then wanted to determine if the unique localization of HCAb2 could be due to differential expression of HSP90 in the tumor cells. To this end, we stained a 24 h time point tumor section with the commercial HSP90 antibody and HCAb2. We observed that the HCAb2 localized tumor cells did not show any changes in the intracellular levels of HSP90 (FIG. 12A-12D), however the levels of cell surface HSP90 could have been increased. To understand the factors that could lead to increased cell surface expression of HSP90, we focused on the function of HSP90 in the tumor cells. HSP90 along with ER chaperones calnexin, calreticulin and protein disulfide isomerase aids in the folding of various proteins. Variation in the levels of the different chaperones could lead to generation of misfolded proteins and in turn lead to stress at the level of protein folding. Previously, it has been shown that the calnexin deficient cells are in a state of constant stress and have constitutively active unfolded protein response. Furthermore, cells that are undergoing stress have been shown to translocate HSP70 from the cytosol to the plasma membrane. This suggests that the cell surface expression of HSP90 similar to HSP70 could be increased in the cells that are undergoing stress. We therefore hypothesized that the xenograft tumor cells that showed HCAb2 localization were highly stressed and thereby had increased HSP90 on the cell surface. In order to test this hypothesis, we stained a 24 h time point MDA-MB-231 tumor section to visualize HCAb2 and calnexin. We observed that the cells that were positive for HCAb2 were specifically negative for calnexin staining (FIG. 7J-7M). Of note, another chaperone marker protein disulfide isomerase (PDI) was unchanged in the HCAb2 positive tumor cells (FIG. 13A-13D). This surprising result suggested that HCAb2 specifically targeted a unique population of cells that could be highly stressed with respect to metabolic or unfolded protein response events. It is unclear as to what could lead to the reduced levels of calnexin in these tumor cells. Immunofluorescence analysis on MDA-MB-231 cells in culture did not reveal any cells that showed reduced levels of calnexin or protein disulfide isomerase (PDI) (FIGS. 14A and 14B), suggesting that the loss of calnexin in the xenograft tumor cells occurred during the formation of the tumor and/or within the tumor microenvironment.

Discussion

The goal of this study was to identify cell surface targeting tumor specific antibodies. To attain this goal, we selected and screened 8 similarly synthesized heavy chain antibodies from a pool of 46 heavy chain antibodies. Owing to the fact that HCAb1 did not bind to a cell surface antigen, nor it showed differential staining between primary human breast normal and tumor tissues, we ruled out HCAb1 as a tumor specific antibody. Using our stringent screening procedure, we identified HCAb2 as a cell surface HSP90 targeting heavy chain antibody. HSP90 is an abundant intracellular chaperone (2-3% of total protein) whose expression increases in stressed cells. Such high levels of HSP90 are postulated to be necessary for efficient folding of a multitude of proteins especially when the cells are undergoing stress. Tumor cells due to their high proliferation rates require higher amounts of HSP90 to ensure appropriate folding of different proteins. HSP90 has been shown to be upregulated in a wide variety of tumors including breast tumors to aid in the folding and stabilization of various tumor associated proteins such as EGFR, mutant B-Raf, mutant BRCA1 and mutant p53. This high expression of HSP90 is therefore an essential requirement for the survival of tumor cells and has been shown to correlate with reduced survival in breast cancer patients. Indeed HSP90 inhibitors have been shown to downregulate the expression of mutant epidermal growth factor receptor in tumors and selectively kill tumor cells. HSP90 inhibitors such as DMAG and 17-AAG have shown promising results, with 17-AAG showing anti-cancer activity in a phase II trial.

In addition to the intracellular localization of HSP90, there have been numerous reports indicating the presence of HSP90 on the cell surface as well as in the extracellular space of tumor cells. HCAb2 showed cytosolic staining in HMEC, MCF7 and MDA-MB-231 cells but showed cell surface staining only on aggressive MDA-MB-231 cells. Indeed HSP90 has been previously shown to be present on the surface of MDA-MB-231 cells. Membrane associated HSP90 has been shown to activate HER-2 and also interact with Cdc37 leading to increased invasiveness of cancer cells. Extracellular HSP90 has also been shown to activate matrix metalloproteinase-2 and plasminogen leading to increased cell motility. The actual mechanism by which HSP90 gets to the cell surface or is released outside the cells is still unclear, with some evidence pointing to the role of exosomes. MDA-MB-231 cells undergoing hypoxic stress have been shown to release increased levels of exosomes. This surge in exosomal release during stress conditions could result in higher amounts of extracellular HSP90 and in turn lead to increased invasiveness of cells. It is interesting to note that HCAb2 demonstrates a punctate staining pattern on MDA-MB-231 cells as well as primary human breast tumor tissues. This punctate pattern could be due to the staining of HSP90 present within the vesicular structures such as exosomes. Further experiments are required to test the possibility that HCAb2 binds to exosomal HSP90.

Considering the significance of membrane bound HSP90 in tumor metastasis, it is imperative to develop novel reagents that can target cell surface HSP90. Indeed DMAG-N-oxide, a cell impermeable HSP90 inhibitor has been shown to inhibit migration of B16 melanoma cells as well as their lung colonization. Along similar lines, we have shown that HCAb2 was also able to reduce the migration of MDA-MB-231 cells in vitro. The advantages of using an antibody such as HCAb2 to target HSP90, instead of an inhibitor would be the possible effector functions of an antibody such as antibody-dependent cell-mediated cytotoxicity and complement-dependent cytotoxicity.

The presence of cell surface HSP90 seems to aid in increasing the invasiveness of the tumor cells. But the reasons for the cell surface localization are not clearly understood. HSP70 is also an intracellular chaperone that is overexpressed in tumors and localizes to the plasma membrane of stressed cells. Similar to HSP70, HSP90 may also be translocated to the plasma membrane of the stressed tumor cells. From our screening analysis on primary human breast tumor tissues, we observed that HCAb2 revealed staining of isolated cells or clusters of cells within the tumors. It could be possible that these isolated or clusters of cells were exposed to different microenvironmental stresses within the tumor tissues leading to increased cell surface expression of HSP90. This trend of HCAb2 binding to stressed cells was also observed in the MDA-MB-231 xenograft tumor cells. HCAb2 localization in the xenograft tumors was restricted to a small subset of tumor cells that were deficient for calnexin. Calnexin along with the other ER chaperones calreticulin and protein disulfide isomerase maintains protein homeostasis and any perturbations to this system could lead to cellular stress. Cellular stresses in the tumors can lead to generation of misfolded proteins, which if left unresolved can activate the unfolded protein response. Previous studies have shown that the cells with reduced calnexin have constitutively active unfolded protein response. This strengthens our argument that HCAb2 localized to highly stressed cells with increased cell surface HSP90.

Calnexin aids in the folding of MHC class I molecules and may also aid in the loading of peptides onto MHC class I molecules. Interestingly, calnexin has been shown to be downregulated in brain metastases of breast tumors compared to unpaired primary breast lesions as well as in metastatic melanoma lesions in comparison to primary melanoma lesions. This down regulation of calnexin can lead to reduced MHC class I molecules on cell surface and has been hypothesized to aid the cells in escaping from adaptive immune response. We believe that HCAb2 is an ideal antibody to target metastatic tumor cells since HCAb2 binds to cell surface HSP90, which is known to aid in invasion as well as to cells that are deficient in calnexin. The relationship between reduced calnexin and increased HSP90 on cell surface needs to be further evaluated. From the preliminary calnexin knockdown experiment (FIG. 11B), it is clear that this relationship is not direct or causal and is probably accentuated in an in vivo tumor setting.

In additional data not shown herein, HCAb2 also showed specific staining on the surface of melanoma cells, bladder tumor cells and ovarian tumor cells in comparison to normal cells. Irrespective of the tumor type, HCAb2 revealed staining of only a subset of tumor cells and identifying the target antigen will probably elucidate the reasons for this specific staining.

Conclusions

In conclusion, we have developed a powerful strategy whereby a library of patient-derived heavy chain antibodies can be screened for those heavy chain antibodies that target tumors specifically. Identification of HCAb2 validates the strength of this research strategy. The antigen for HCAb2 was found to be HSP90 and HCAb2 bound to a unique subset of xenograft tumor cells that were calnexin negative. This raises interesting questions as to the connection between reductions in the levels of calnexin, microenvironment or oncogene induced stress and the resultant increased cell surface HSP90. In addition, HCAb2 can be a unique reagent to target aggressive human tumor cells in vivo and may be useful for therapeutic and diagnostic applications.

Example 8: Expression of Light Chains

Human Light Chain lambda and kappa libraries were synthesized from the same lymph node sample as the HCAb2 using oligo primers aligned to the 5' amino acid sequence and 3' to the light chain constant regions. Amplicons were cloned into TOPO-TA vectors and sequenced. Clustering of the individual light chain sequences showed Lambda clusters being prevalent and the pool of 4 light chains were representative clones from each of 4 major clusters (clones ≥6). This pool of light chain sequences was co-expressed with HCAB2 and the resulting antibody molecules were evaluated to confirm efficiency, specificity and affinity to target tumor cells compared to non-tumor cells. The light chains are SEQ ID Nos; 8-11 and alignments are provided in FIG. 14.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. An isolated antibody or antigen-binding fragment comprising a heavy chain variable region comprising three heavy chain complementary determining regions (HCDRs), wherein the sequence of HCDR1 is GYRLSELS (SEQ ID NO: 1), the sequence of HCDR2 is ISGWDGNT (SEQ ID NO: 2), and the sequence of HCDR3 is ARASGYNY(SEQ ID NO: 3), wherein the isolated antibody or antigen-binding fragment specifically binds human HSP90.

2. The isolated antibody or antigen-binding fragment of claim 1, wherein the isolated antibody or antigen-binding fragment specifically binds human HSP90beta.

3. The isolated antibody or antigen-binding fragment of claim 1, comprising a heavy chain region having at least 95% sequence identity with SEQ ID NO: 4.

4. The isolated antibody or antigen-binding fragment of claim 3, comprising a heavy chain region having SEQ ID NO: 4.

5. The isolated antibody or antigen-binding fragment of claim 1, wherein the antibody is a single chain antibody consisting of the heavy chain variable region as defined in claim 1.

6. The isolated antibody or antigen-binding fragment of claim 5, wherein the single chain antibody consists of a heavy chain region having at least 95% sequence identity with SEQ ID NO: 4.

7. The isolated antibody or antigen-binding fragment of claim 6, wherein the single chain antibody consists of a heavy chain region having SEQ ID NO: 4.

8. The isolated antibody or antigen-binding fragment of claim 1, further comprising an Fc region fused to the heavy chain variable region.

9. The isolated antibody or antigen-binding fragment of claim 8, further comprising a light chain.

10. The isolated antibody or antigen-binding fragment of claim 9, wherein the light chain comprises SEQ ID NO:5, SEQ ID NO: 6, SEQ ID NO: 7, or SEQ ID NO: 8.

11. The isolated antibody or antigen-binding fragment of claim 1, further comprising an attached detectable moiety or therapeutic agent.

12. A pharmaceutical composition comprising the isolated antibody or antigen-binding fragment of claim 1 and a pharmaceutically acceptable carrier.

13. A method of detecting the presence of HSP90 in a biological sample, the method comprising contacting the biological sample with the isolated antibody or antigen-binding fragment of claim 1 and detecting binding of the isolated antibody or antigen-binding fragment to HSP90, wherein binding indicates the presence of HSP90 in the sample.

14. The method of claim 13, wherein the isolated antibody or antigen-binding fragment specifically binds human HSP90 beta.

15. The method of claim 13, wherein detecting comprises performing an immunoassay.

16. The method of claim 15, wherein the immunoassay is a Western blot, immunofluorescence assay, an enzymatic immunoassay, an enzyme-linked immunosorbent assay, immunohistochemistry, immunoprecipitation, immunoelectrophoresis, a dipstick, an assay strip radioimmunometric assay, a tissue microarray assay, or an immunoturbidimetric assay.

17. The method of claim 16, wherein the immunofluorescence assay uses confocal microscopy detection.

\* \* \* \* \*